US007823761B2

(12) United States Patent
Boyden et al.

(10) Patent No.: US 7,823,761 B2
(45) Date of Patent: Nov. 2, 2010

(54) MANEUVERABLE SURGICAL STAPLER

(75) Inventors: Edward S. Boyden, Cambridge, MA (US); Roderick A. Hyde, Redmond, WA (US); Muriel Y. Ishikawa, Livermore, CA (US); Eric C. Leuthardt, St. Louis, MO (US); Nathan P. Myhrvold, Medina, WA (US); Dennis J. Rivet, Portsmouth, VA (US); Michael A. Smith, Phoenix, AZ (US); Clarence T. Tegreene, Bellevue, WA (US); Thomas A. Weaver, San Mateo, CA (US); Charles Whitmer, North Bend, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 89 days.

(21) Appl. No.: 11/894,044

(22) Filed: Aug. 17, 2007

(65) Prior Publication Data
US 2008/0283574 A1 Nov. 20, 2008

Related U.S. Application Data

(63) Continuation-in-part of application No. 11/804,219, filed on May 16, 2007.

(51) Int. Cl.
*A61B 17/068* (2006.01)
(52) U.S. Cl. ................ 227/175.1; 227/19; 606/139; 606/219
(58) Field of Classification Search ............ 227/19, 227/176.1, 175.1, 180.1, 179.1; 606/139, 606/219
See application file for complete search history.

(56) References Cited

U.S. PATENT DOCUMENTS 3,991,767 A 11/1976 Miller, Jr. et al.
4,505,414 A 3/1985 Filipi
4,635,638 A 1/1987 Weintraub et al.
4,655,222 A 4/1987 Florez et al.

(Continued)

FOREIGN PATENT DOCUMENTS

WO WO/00/51566 9/2000

OTHER PUBLICATIONS

Alfieri, Ottavio MD, Elefteriades, John A. MD., Chapolini, Robert J. MC, Steckel, Robert DVM, Allen, William J, PE, Reed, Scott W. BS, Schreck, Stefan PhD, "Novel Suture Device for Beating-heart Mitral Leaflet Approximation", Annals of Thoracic Surgery, dated 2002, vol. 74, pp. 1488-1493; The Society of Thoracic Surgeons; located at: http:/ats.ctsnetjournals.org/cgi/content/full/74/5/1488.

(Continued)

*Primary Examiner*—Scott A. Smith

(57) ABSTRACT

Embodiments include a surgical device and a method. An embodiment of the surgical instrument includes at least one grasping jaw, the at least one grasping jaw being adapted to deliver surgical staples by a force generated from a force generator mechanism that is contained within the at least one grasping jaw or is in a proximity to the at least one grasping jaw. Another embodiment includes at least one grasping jaw, at least one delivery mechanism adapted to deliver surgical fasteners, the delivery mechanism being located in a proximity to or contained within the at least one grasping jaw, the surgical fasteners containing at least one shape-transforming material, at least one sensor, at least one chemical tissue sealant and at least one cutter. A method includes: grasping a body tissue with at least one grasping jaw, adjusting a configuration of the grasping in response to a signal or a datum or an image, and releasing a surgical staple/fastener in response to the signal, datum or image.

23 Claims, 25 Drawing Sheets

U.S. PATENT DOCUMENTS

| | | |
|---|---|---|
| 4,669,473 A | 6/1987 | Richards et al. |
| 4,706,689 A | 11/1987 | Man |
| 4,754,909 A | 7/1988 | Barker et al. |
| 4,767,044 A | 8/1988 | Green |
| 4,836,205 A | 6/1989 | Barrett |
| 4,941,623 A | 7/1990 | Pruitt |
| 5,027,834 A | 7/1991 | Pruitt |
| 5,081,282 A | 1/1992 | Jones et al. |
| 5,176,647 A | 1/1993 | Knoepfler |
| 5,188,274 A | 2/1993 | Moeinzadeh et al. |
| 5,197,649 A | 3/1993 | Bessler et al. |
| 5,217,472 A | 6/1993 | Green et al. |
| 5,222,962 A | 6/1993 | Burkhart |
| 5,263,927 A | 11/1993 | Shlain |
| 5,324,307 A | 6/1994 | Jarrett et al. |
| 5,368,015 A | 11/1994 | Wilk |
| 5,383,880 A | 1/1995 | Hooven |
| 5,383,895 A | 1/1995 | Holmes et al. |
| 5,395,033 A | 3/1995 | Byrne et al. |
| 5,413,107 A | 5/1995 | Oakley et al. |
| 5,417,684 A | 5/1995 | Jackson et al. |
| 5,431,645 A | 7/1995 | Smith et al. |
| 5,445,304 A | 8/1995 | Plyley et al. |
| 5,462,215 A | 10/1995 | Viola et al. |
| 5,472,427 A | 12/1995 | Rammler |
| 5,518,164 A | 5/1996 | Hooven |
| 5,520,700 A | 5/1996 | Beyar et al. |
| 5,549,636 A | 8/1996 | Li |
| 5,550,172 A | 8/1996 | Regula et al. |
| 5,578,031 A | 11/1996 | Wilk et al. |
| 5,582,611 A | 12/1996 | Tsuruta et al. |
| 5,609,560 A | 3/1997 | Ichikawa et al. |
| 5,609,607 A | 3/1997 | Hechtenberg et al. |
| 5,613,973 A | 3/1997 | Jackson et al. |
| 5,624,452 A | 4/1997 | Yates |
| 5,667,517 A | 9/1997 | Hooven |
| 5,683,401 A | 11/1997 | Schmieding et al. |
| 5,700,901 A | 12/1997 | Hurst et al. |
| 5,702,409 A | 12/1997 | Rayburn et al. |
| 5,709,693 A | 1/1998 | Taylor |
| 5,728,121 A | 3/1998 | Bimbo et al. |
| 5,735,862 A | 4/1998 | Jennings et al. |
| 5,782,397 A | 7/1998 | Koukline |
| 5,782,845 A | 7/1998 | Shewchuk |
| 5,807,261 A | 9/1998 | Benaron et al. |
| 5,810,855 A | 9/1998 | Rayburn et al. |
| 5,814,022 A | 9/1998 | Antanavich et al. |
| 5,814,054 A | 9/1998 | Kortenbach et al. |
| 5,860,426 A | 1/1999 | Kleiman |
| 5,900,245 A | 5/1999 | Sawhney et al. |
| 5,922,009 A | 7/1999 | Epstein et al. |
| 5,935,149 A | 8/1999 | Ek |
| 5,965,880 A | 10/1999 | Wolf et al. |
| 6,015,382 A | 1/2000 | Zwart et al. |
| 6,045,560 A | 4/2000 | McKean et al. |
| 6,063,095 A | 5/2000 | Wang et al. |
| 6,081,738 A | 6/2000 | Hinohara et al. |
| 6,102,844 A | 8/2000 | Ravins et al. |
| 6,113,611 A | 9/2000 | Allen et al. |
| 6,126,591 A | 10/2000 | McGarry et al. |
| 6,126,658 A | 10/2000 | Baker |
| 6,139,556 A | 10/2000 | Kontos |
| 6,221,068 B1 | 4/2001 | Fried et al. |
| 6,267,761 B1 | 7/2001 | Ryan |
| 6,302,311 B1 | 10/2001 | Adams et al. |
| 6,319,942 B1 | 11/2001 | Perricone |
| 6,332,889 B1 | 12/2001 | Sancoff et al. |
| 6,338,737 B1 | 1/2002 | Toledano |
| 6,371,910 B1 | 4/2002 | Zwart et al. |
| 6,428,463 B1 | 8/2002 | Ravins et al. |
| 6,432,035 B1 | 8/2002 | Ravins et al. |
| 6,436,107 B1* | 8/2002 | Wang et al. .................. 606/139 |
| 6,443,973 B1 | 9/2002 | Whitman |
| 6,461,355 B2 | 10/2002 | Svejkovsky et al. |
| 6,508,755 B1 | 1/2003 | Ravins et al. |
| 6,569,173 B1 | 5/2003 | Blatter et al. |
| 6,589,239 B2 | 7/2003 | Khandkar et al. |
| 6,592,508 B1 | 7/2003 | Ravins et al. |
| 6,623,494 B1 | 9/2003 | Blatter |
| 6,638,283 B2 | 10/2003 | Thal |
| 6,648,900 B2 | 11/2003 | Fleischman et al. |
| 6,652,543 B2 | 11/2003 | Spence et al. |
| 6,652,544 B2 | 11/2003 | Houser et al. |
| 6,663,643 B2 | 12/2003 | Field |
| 6,716,233 B1 | 4/2004 | Whitman |
| 6,720,710 B1 | 4/2004 | Wenzel et al. |
| 6,726,694 B2 | 4/2004 | Blatter et al. |
| 6,743,229 B2 | 6/2004 | Buysse et al. |
| 6,756,518 B2 | 6/2004 | Gruskin et al. |
| 6,773,409 B2 | 8/2004 | Truckai et al. |
| 6,805,273 B2 | 10/2004 | Bilotti et al. |
| 6,830,573 B2 | 12/2004 | Strong et al. |
| 6,843,403 B2 | 1/2005 | Whitman |
| 6,849,071 B2 | 2/2005 | Whitman et al. |
| 6,858,035 B2 | 2/2005 | Whayne |
| RE38,708 E | 3/2005 | Bolanos et al. |
| 6,860,895 B1 | 3/2005 | Akerfeldt et al. |
| 6,872,214 B2 | 3/2005 | Sonnenschein et al. |
| 6,929,644 B2 | 8/2005 | Truckai et al. |
| 6,932,810 B2 | 8/2005 | Ryan |
| 7,059,509 B2 | 6/2006 | Brown |
| 7,077,856 B2 | 7/2006 | Whitman |
| 7,080,769 B2 | 7/2006 | Vresh et al. |
| 7,083,613 B2 | 8/2006 | Treat |
| 7,083,631 B2 | 8/2006 | Houser et al. |
| 7,097,089 B2 | 8/2006 | Marczyk |
| 7,101,373 B2* | 9/2006 | Dycus et al. .................. 606/51 |
| 7,135,029 B2 | 11/2006 | Makin et al. |
| 7,142,741 B2 | 11/2006 | Osborne |
| 7,150,097 B2 | 12/2006 | Sremcich et al. |
| 7,150,747 B1 | 12/2006 | McDonald et al. |
| 7,156,863 B2 | 1/2007 | Sonnenschein et al. |
| 7,160,299 B2 | 1/2007 | Baily |
| 7,179,258 B2 | 2/2007 | Buysse et al. |
| 7,195,465 B2 | 3/2007 | Kane et al. |
| 7,208,005 B2 | 4/2007 | Frecker et al. |
| 7,214,230 B2 | 5/2007 | Brock et al. |
| 7,225,963 B2 | 6/2007 | Scirica |
| 7,238,195 B2 | 7/2007 | Viola |
| 7,288,099 B2 | 10/2007 | Deem et al. |
| 7,300,450 B2 | 11/2007 | Vleugels et al. |
| 7,306,614 B2 | 12/2007 | Weller et al. |
| 7,431,730 B2 | 10/2008 | Viola |
| 7,540,870 B2 | 6/2009 | Babaev |
| 2002/0010482 A1 | 1/2002 | Watt |
| 2002/0055701 A1 | 5/2002 | Fischell et al. |
| 2002/0087169 A1 | 7/2002 | Brock et al. |
| 2002/0133225 A1 | 9/2002 | Gordon |
| 2002/0173745 A1 | 11/2002 | Santini, Jr. et al. |
| 2002/0190093 A1 | 12/2002 | Fenton, Jr. |
| 2002/0193656 A1 | 12/2002 | Ravins et al. |
| 2003/0008011 A1 | 1/2003 | Mershon |
| 2003/0065358 A1 | 4/2003 | Frecker et al. |
| 2003/0093119 A1 | 5/2003 | Zhao et al. |
| 2003/0199924 A1 | 10/2003 | Coleman et al. |
| 2003/0216754 A1 | 11/2003 | Kraemer et al. |
| 2003/0216778 A1 | 11/2003 | Weadock |
| 2004/0034357 A1 | 2/2004 | Beane et al. |
| 2004/0094598 A1 | 5/2004 | Geiste et al. |
| 2004/0102804 A1 | 5/2004 | Chin |
| 2004/0111115 A1 | 6/2004 | Maw |
| 2004/0167572 A1 | 8/2004 | Roth et al. |
| 2004/0241211 A9 | 12/2004 | Fischell et al. |
| 2005/0116008 A1 | 6/2005 | Thornton et al. |

| | | |
|---|---|---|
| 2005/0119669 A1 | 6/2005 | Demmy |
| 2005/0145671 A1 | 7/2005 | Viola |
| 2005/0184121 A1 | 8/2005 | Heinrich |
| 2005/0184123 A1 | 8/2005 | Scirica |
| 2005/0184125 A1 | 8/2005 | Marczyk |
| 2005/0209564 A1 | 9/2005 | Bonner et al. |
| 2005/0228443 A1 | 10/2005 | Yassinzadeh |
| 2005/0230453 A1 | 10/2005 | Viola |
| 2005/0274384 A1 | 12/2005 | Tran et al. |
| 2005/0274768 A1 | 12/2005 | Cummins et al. |
| 2005/0281860 A1 | 12/2005 | Fischell et al. |
| 2006/0025817 A1 | 2/2006 | Ortiz et al. |
| 2006/0041273 A1 | 2/2006 | Ortiz et al. |
| 2006/0079925 A1 | 4/2006 | Kerr |
| 2006/0095134 A1 | 5/2006 | Trieu et al. |
| 2006/0105453 A1 | 5/2006 | Brenan et al. |
| 2006/0147479 A1 | 7/2006 | Atkin et al. |
| 2006/0185682 A1 | 8/2006 | Marczyk |
| 2006/0190027 A1 | 8/2006 | Downey |
| 2006/0217750 A1 | 9/2006 | Ghannoum |
| 2006/0271041 A1 | 11/2006 | Eder et al. |
| 2007/0021738 A1 | 1/2007 | Hasser et al. |
| 2007/0029364 A1 | 2/2007 | Kruszynski et al. |
| 2007/0102453 A1 | 5/2007 | Morgan et al. |
| 2007/0170225 A1 | 7/2007 | Shelton, IV et al. |
| 2007/0179525 A1 | 8/2007 | Frecker et al. |
| 2007/0187454 A1 | 8/2007 | Scirica |
| 2008/0004634 A1 | 1/2008 | Farritor et al. |
| 2008/0065109 A1 | 3/2008 | Larkin |
| 2008/0065110 A1 | 3/2008 | Duval et al. |
| 2008/0164296 A1 | 7/2008 | Shelton et al. |
| 2008/0185419 A1 | 8/2008 | Smith et al. |
| 2008/0190989 A1 | 8/2008 | Crews et al. |

OTHER PUBLICATIONS

Deshpande, Mandar and Saggere, Laxman, "Modeling and Design of an Optically Powered Microactuator for a Microfluidic Dispenser", Journal of Mechanical Design, Jul. 2005, vol. 127, Issue 4, pp. 825-836; ASME; located at http://www.me.org/terms/Terms_e.cfm.

U.S. Appl. No. 11/998,844, Nov. 30, 2007, Boyden et al.
U.S. Appl. No. 11/981,825, Oct. 30, 2007, Boyden et al.
U.S. Appl. No. 11/977,746, Oct. 25, 2007, Boyden et al.
U.S. Appl. No. 11/906,165, Sep. 28, 2007, Boyden et al.
U.S. Appl. No. 11/901,955, Sep. 18, 2007, Boyden et al.
U.S. Appl. No. 11/987,974, Aug. 31, 2007, Boyden et al.
U.S. Appl. No. 11/985,644, Aug. 23, 2007, Boyden et al.
U.S. Appl. No. 11/818,884, Jun. 15, 2007, Boyden et al.
U.S. Appl. No. 11/804,219, May 16, 2007, Boyden et al.

Gotoh, Masashi, Okamoto, Taku, Tamamoto, Yasumichi, and Yokomise, Hiroyasu, "Real Time Imaging and Quantitative Evaluation of the Emphysematous Lung by Infrared Thoracoscopy in Experimental Dogs", ASAIO Journal dated Mar./Apr. 2005, vol. 51(2), pp. 148-151; ASAIO Journal Abstract located at: lattp://www.asaiojournal.com/pt/re/asaio/abstract,00002480-2005030 (abstract only).

Julian, T.B. And Ravitch, M.M., "Closure of the Urinary Bladder with Stainless Steel Staples", Annals of Surgery, dated Aug. 1986, vol. 204(2), pp. 186-192; located at http://www.pubmedcentral.nih.gov/articlerender.fcgi?artid=1251261.

* cited by examiner

MANEUVERABLE SURGICAL STAPLER

CROSS-REFERENCE TO RELATED APPLICATIONS

The present application is related to and claims the benefit of the earliest available effective filing date from the following listed application (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications

For purposes of the USPTO extra-statutory requirements, the present application constitutes a continuation-in-part of U.S. patent application Ser. No. 11/804,219, entitled STEERABLE SURGICAL STAPLER, naming Edward S. Boyden, Roderick A. Hyde, Muriel Y. Ishikawa, Eric C. Leuthardt, Nathan P. Myhrvold, Dennis J. Rivet, Michael A. Smith, Clarence T. Tegreene, Thomas A. Weaver, Charles Whitmer, Lowell L. Wood, Jr., and Victoria Y. H. Wood as inventors, filed May 16, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present application relates, in general, to devices, methods or systems for treatment or management of disease, disorders, or conditions.

SUMMARY

An embodiment of a surgical instrument comprises a surgical stapler. In one embodiment, the surgical stapler comprises at least one grasping jaw, the at least one grasping jaw being adapted to deliver surgical staples by a force generated from a force generator mechanism that is contained within the at least one grasping jaw or is in a proximity to the at least one grasping jaw. In a further embodiment, the at least one grasping jaw is configured to movably operate in an opposing manner with respect to at least one other grasping jaw. In another embodiment, at least one grasping jaw is configured to operably mate with at least one other grasping jaw. In yet another embodiment, at least one grasping jaw is configured to serve as an anvil for forming an interaction surface between at least one surgical staple and bodily tissues, the forming being facilitated by reversible mating and unmating of the anvil with an opposite grasping jaw. Furthermore, at least one grasping jaw may form an annular grasp around a body tissue.

In one embodiment, the surgical stapler has a force generated from a force generator mechanism is communicated to a medium resulting in the release of at least one surgical staple. The force may further result in delivery of one or more linear rows of surgical staples. The force generating mechanism may further include at least one of a pressurized gas canister/cartridge, a spring, a lever, an explosive charge, a piezoelectric actuator, an electric motor, an electroactive polymer or a solenoid.

In another embodiment, the surgical stapler comprises at least one energy module. The energy module may include at least one of a battery, a capacitor, a fuel cell, a mechanical energy storage device, or a fluid energy storage device. Furthermore, the energy module may be located in proximity to at least one grasping jaw or within at least one grasping jaw. In a further embodiment, the energy module transmits energy through a medium containing at least one of the following: a wire, a tube, an optical fiber or a waveguide. Alternatively, the energy module transmits energy through a wireless device.

In one embodiment, the surgical stapler may include a flexually deformable and steerable shaft connected to at least one grasping jaw. The shaft may contain at least one shape-transforming material, which may include a shape memory alloy. In other embodiments, the shape memory alloy includes at least one of the following components: titanium, nickel, zinc, copper, aluminum, cadmium, platinum, iron, manganese, cobalt, gallium or tungsten. The shape memory alloy may also include Nitinol™ or an electro-active polymer. Furthermore, at least one shape-transforming material includes at least one mechanically reconfigurable material. In an embodiment, the surgical instrument further comprises at least one sensor. At least one sensor may be disposed in at least one grasping jaw of the surgical instrument. Alternatively, the at least one sensor may be disposed in proximity to at least one grasping jaw. In one embodiment, the at least one sensor includes an image-acquisition device. The image-acquisition device may include at least one of the following: a camera, a charge coupled device, an X-ray receiver, an acoustic energy receiver, a photodetector, an electromagnetic energy receiver or an imaging device.

In an embodiment of the surgical stapler, the sensor includes an illumination device that is operably coupled to at least one image-acquisition device. In a further embodiment, the image-acquisition device is wirelessly coupled to at least one visual display. The at least one sensor may include a data-transmission device. In yet another embodiment, at least one sensor includes a proximity detector. The proximity detector may be adapted to detect proximity of a biological tissue to the surgical instrument. In an embodiment, the proximity detector includes an electromagnetic energy emitter or an electromagnetic energy receiver. In yet another embodiment, proximity detector includes an acoustic energy emitter and an acoustic energy receiver. In another embodiment, the proximity detector includes a point source emitter or a source illuminator. In an alternative embodiment, point source emitter or a source illuminator is operably coupled to at least one image acquisition device. The point source emitter or a source illuminator may include at least one of an ultrasonic source, an acoustic source, a visible source, an ultraviolet source, a gamma ray source, an X-ray source or an infrared source. Furthermore, the point source or source illuminator may be operably configured within a grasping jaw of the surgical instrument. In one embodiment, the proximity detector includes a communication medium for communication with at least one image display. In another embodiment, the proximity detector may also include at least one image-transmission device or one data-transmission device. In yet another embodiment, the proximity detector is wirelessly coupled to at least one image display.

In an embodiment, at least one sensor provides a feedback signal, a datum or an image to a human or robotic user. Furthermore, at least one sensor provides a force feedback signal to a force generator mechanism. Another embodiment provides at least one sensor that communicates a signal, a datum or an image regarding status of the number of staples in the surgical instrument. Furthermore, at least one sensor may provide a signal, a datum or an image regarding functional status or malfunctional status of the surgical instrument.

In another embodiment, the surgical instrument further comprises at least one cutter. In yet another embodiment the cutter may be an optical cutter or a laser-mediated cutting device or an electro-thermal cutting device. In a further embodiment, at least one cutter may include a blade, a knife or an edge. An embodiment provides that at least one cutter is operably coupled to at least one grasping jaw.

The surgical instrument may be further configured to deliver a chemical tissue sealant. The chemical tissue sealant may be housed inside at least one grasping jaw. An embodiment provides that the chemical tissue sealant be a biocompatible or a biodegradable sealant. Furthermore, the chemical sealant is delivered in a proximity to at least one staple, and is preferably delivered between at least two adjacent layers of body tissue. In some embodiments, surgical staples may include fasteners, pins or ties.

An embodiment of the surgical instrument provides at least one grasping jaw. In another embodiment, the at least one grasping jaw comprises a delivery mechanism adapted to deliver surgical fasteners. In an embodiment, the delivery mechanism may be located in a proximity to at least one grasping jaw. In an alternative embodiment, the delivery mechanism may be contained within at least one grasping jaw. Furthermore, the surgical fasteners may contain at least one shape-transforming material. The surgical instrument may optionally include at least one sensor. In some embodiments, the at least one grasping jaw is configured to movably operate in an opposing manner with respect to at least one other grasping jaw. In an alternative embodiment, at least one grasping jaw is configured to operably mate with at least one other grasping jaw. In yet another embodiment, at least one grasping jaw is configured to serve as an anvil for forming an interaction surface between at least one surgical fastener and bodily tissues, the forming being facilitated by reversible mating and unmating of the anvil with an opposite grasping jaw. Moreover, at least one grasping jaw may form an annular grasp around a body tissue. In one embodiment, the delivery mechanism utilizes a force generated from a force generator mechanism contained within or in a proximity to at least one grasping jaw. Furthermore, the delivery mechanism results in delivery of one or more linear rows of surgical fasteners. An embodiment provides that the force generated from the force generator mechanism includes at least one of a pressurized gas canister/cartridge, a spring, a lever, an explosive charge, a piezoelectric actuator, an electric motor, an electroactive polymer, a hydraulic force, a pneumatic force, or a solenoid.

An aspect of the invention includes a surgical instrument comprising a flexually deformable and steerable shaft operably connected to at least one grasping jaw having a force generator mechanism that is contained within the at least one grasping jaw or is in a proximity to the at least one grasping jaw. The surgical instrument may further comprise of at least one grasping jaw that is independently maneuverable from an attached shaft or sheath. Additionally or alternatively, the flexually deformable and steerable shaft may be enclosed in a bendable and steerable tube or a sheath. Furthermore, in an embodiment, the flexually deformable and steerable shaft may be controllably deformable and steerable to permit a high degree of maneuverability of the surgical instrument. Alternatively or additionally, the flexually deformable and steerable shaft may contain at least one shape-transforming material. In one embodiment, the at least one shape-transforming material contains a shape memory alloy. In another embodiment, the shape memory alloy includes at least one of titanium, nickel, zinc, copper, aluminum, cadmium, platinum, iron, manganese, cobalt, gallium or tungsten. Additionally or alternatively, the at least one shape-transforming material may be preconfigured to a particular application and body part geometry. Furthermore, the at least one shape-transforming material may assume a different shape compared to an original preconfigured shape upon insertion of the surgical instrument into a body to conform to an optimal orientation. The flexually deformable and steerable shaft may include the shape memory alloy Nitinol™. In yet another embodiment, the flexually deformable and steerable shaft may contain at least one shape-transforming material that includes an electro-active polymer. In still another embodiment, the at least one shape-transforming material includes at least one mechanically reconfigurable material. In one embodiment, the flexually deformable and steerable shaft may be controllably deformable and steerable to permit a high degree of maneuverability of the surgical instrument that includes controllable deformation of the shaft that is mediated by at least one of a temperature profile, a pressure profile, an electrical circuitry, a magnetic profile, an acoustic wave profile or an electromagnetic radiation profile. The maneuverability of the surgical instrument includes maneuverability around anatomical corners or difficult-to-reach anatomical body parts that are normally inaccessible on a straight trajectory. In an embodiment, the flexually deformable and steerable shaft that is being controllably deformable to permit a high degree of maneuverability of the surgical instrument includes bending the shaft in real time to navigate within a body space. In still another embodiment, the flexually deformable and steerable shaft returns to an original shape or configuration for easy removal from a body. In yet another embodiment, the surgical instrument may include at least one grasping jaw having a proximity detector. The proximity detector may be adapted to detect whether a biological tissue is within grasping distance of the grasping jaw. Furthermore, the proximity detector may also be adapted to detect whether a biological tissue is fully grasped by the grasping jaw. In an embodiment, the proximity detector is operably configured to assess whether an entire bodily organ or a portion of a bodily organ is fully or partly grasped within said grasping jaw. Alternatively or additionally, the grasping jaw may be fully redeployable following at least one grasp-release cycle in a grasping operation of a biological tissue. Additionally or alternatively, the surgical instrument may be a surgical stapler that is adapted to deliver biodegradable or non-biodegradable staples, fasteners, pins or ties.

An aspect of the invention includes a surgical instrument comprising at least one grasping jaw; a force receiver adapted to receive manual force from a user; and an actuation mechanism responsive to the manual force to produce a jaw-laden force without mechanical coupling of the manual force to the grasping jaw. In an embodiment, the surgical instrument further includes the force receiver includes at least one sensor. In yet another embodiment, the at least one sensor is operably coupled to the actuation mechanism. Furthermore, the at least one sensor receives a signal from the actuation mechanism through a wireless medium. In another embodiment, the surgical instrument includes the at least one sensor that transmits a signal to the actuation mechanism through a wireless medium. In still another embodiment, the surgical instrument includes a user-activated sensory-device, tactile-device or audio-sensitive device that transmits a signal to the force receiver. The user-activated sensory, tactile or audio-sensitive device may be a manual trigger, a pushbutton, a latch, a lever, a voice activated device, a touch-sensitive device, a breath-activated device etc. In another embodiment, the surgical instrument includes a jaw-laden force without mechanically coupling the force to the grasping jaw. The force may be carried through a wireless medium, an ethereal medium or other intangible media. In another embodiment, the actuation mechanism converts a manual force from the force receiver into the jaw-laden force. In yet another embodiment, the jaw-laden force results in release of at least one surgical stapler or surgical; fastener.

The following embodiments are directed to a surgical instrument that is adapted to deliver surgical fasteners and may contain at least one shape-transforming material or at least one sensor.

In an alternative embodiment of the surgical instrument that is adapted to deliver surgical fasteners, the surgical instrument further comprises at least one energy module that includes at least one of a battery, a capacitor, a fuel cell, a mechanical energy storage device, or a fluid energy storage device. At least one energy module may be located within or in a proximity to the at least one grasping jaw. In an embodiment, least one energy module is located outside the at least one grasping jaw but is within a portion of the surgical instrument. An embodiment provides that at least one energy module is located outside the at least one grasping jaw.

An embodiment of the surgical instrument that is adapted to deliver surgical fasteners provides that at least one energy module transmits energy through a medium containing at least one of a wire, a tube, an optical fiber or a waveguide. Alternately, at least one energy module transmits energy through a wireless device.

In one embodiment of the surgical instrument that is adapted to deliver surgical fasteners, at least one fastener contains one shape-transforming material. The shape transforming material may contain a shape memory alloy. The shape memory alloy may include at least one of titanium, nickel, zinc, copper, aluminum, cadmium, platinum, iron, manganese, cobalt, gallium or tungsten. Alternatively, the shape memory alloy includes Nitinol™ or an electro-active polymer. Alternative embodiments call for at least one shape-transforming material to include at least one mechanically reconfigurable material.

In an embodiment of the surgical instrument that is adapted to deliver surgical fasteners, the surgical instrument has at least one sensor that is disposed within at least one grasping jaw. Alternatively, at least one sensor may be disposed in a proximity to at least one grasping jaw. In an embodiment, at least one sensor includes an image-acquisition device. The image-acquisition device may include at least one of a camera, a charge coupled device, an X-ray receiver, an acoustic energy receiver, an electromagnetic energy receiver or an imaging device. In an embodiment, the image-acquisition device is wirelessly coupled to at least one visual display. The sensor may include an illumination device that is operably coupled to an image-acquisition device. Alternatively, at least one sensor includes a data-transmission device. In an embodiment, the proximity detector is adapted to detect the proximity of a biological tissue to the surgical instrument. In a further embodiment, the proximity detector includes an electromagnetic energy emitter or an electromagnetic energy receiver. In yet another embodiment, the proximity detector includes an acoustic energy emitter and an acoustic energy receiver. In an embodiment, the proximity detector includes a point source emitter or a source illuminator. The point source emitter or a source illuminator, in some embodiment are operably coupled to at least one image acquisition device. Furthermore, the point source emitter or a source illuminator include at least one of an ultrasonic source, an acoustic source, a visible source, an ultraviolet source, a gamma ray source, an X-ray source or an infrared source. Alternatively or additionally, point source emitter or a source illuminator are operably configured within a grasping jaw of the surgical instrument. The proximity detector may include a communication medium for communication with at least one image display. In one embodiment, the proximity detector includes at least one image-transmission device. In a further embodiment, the proximity detector includes at least one data-transmission device. Furthermore, the proximity detector is wirelessly coupled to at least one image display.

In an embodiment of the surgical instrument that is adapted to deliver surgical fasteners, the surgical instrument comprises at least one sensor that provides a feedback signal, a datum or an image to a human or robotic user. Additionally, at least one sensor provides a force feedback signal to the delivery mechanism. At least one sensor may provide a signal, a datum or an image regarding status of the number of fasteners in the surgical instrument. Furthermore, at least one sensor provides a signal, a datum or an image regarding functional status or malfunctional status of the surgical instrument.

In another embodiment of the surgical instrument that is adapted to deliver surgical fasteners, the surgical instrument further comprises at least one cutter. Additionally, in some embodiments, at least one cutter is an optical cutter. In a further embodiment, the optical cutter may be a laser-mediated cutting device. The surgical instrument may have at least one cutter that is an electro-thermal cutter. Furthermore at least one cutter may include one of a blade, a knife or an edge. In an embodiment, at least one cutter is operably coupled to at least one grasping jaw.

In an embodiment of the surgical instrument that is adapted to deliver surgical fasteners, the instrument may be further configured to deliver a chemical tissue sealant. In another embodiment, the chemical tissue sealant is housed inside at least one grasping jaw. In an alternative embodiment, the chemical tissue sealant is a biocompatible chemical tissue sealant. Furthermore the sealant may be a biodegradable chemical tissue sealant. Additional embodiments may provide for a chemical tissue sealant that is delivered in a proximity to at least one fastener. Further, the chemical tissue sealant may be delivered between at least two adjacent layers of body tissue.

In some embodiments of the surgical instrument that is adapted to deliver fasteners, the surgical instrument may deliver surgical fasteners including staples, pins or ties. In another embodiment, the surgical instrument may comprise at least one grasping jaw having a curvature that conforms to a body tissue or more than two grasping jaws. Further variants of embodiments of the surgical instrument may comprise of a flexually deformable and steerable shaft connected to at least one grasping jaw. In an embodiment, the flexually deformable and steerable shaft contains at least one shape-transforming material. In some embodiments, at least one shape-transforming material contains a shape memory alloy. The shape memory alloy may include at least one of titanium, nickel, zinc, copper, aluminum, cadmium, platinum, iron, manganese, cobalt, gallium or tungsten. In one embodiment, shape memory alloy includes Nitinol™ or an electro-active polymer. At least one shape-transforming material may include at least one mechanically reconfigurable material in an embodiment of the surgical instrument.

An aspect of a surgical instrument may comprise at least one grasping jaw and at least one delivery mechanism that may be adapted to deliver surgical fasteners. Furthermore, the delivery mechanism may be located in a proximity to or may be contained within the at least one grasping jaw. Moreover, the surgical fasteners may contain at least one shape-transforming material or at least one chemical tissue sealant. In an embodiment, at least one grasping jaw is configured to movably operate in an opposing manner with respect to at least one other grasping jaw. Furthermore, at least one grasping jaw is configured to operably mate with at least one other grasping jaw. Additionally, at least one grasping jaw may be configured to serve as an anvil for forming an interaction surface between at least one surgical fastener and bodily tissues, the forming being facilitated by reversible mating and unmating of the anvil with an opposite grasping jaw. In another embodiment, at least one grasping jaw may form an annular grasp around a body tissue. In yet another embodiment, the delivery mechanism utilizes a force generated from a force generator mechanism contained within or in proximity to at least one grasping jaw. Furthermore, the delivery mechanism results in delivery of one or more linear rows of surgical fasteners.

The following embodiments are directed to a surgical instrument that is adapted to deliver surgical fasteners and may contain at least one shape-transforming material or at least one chemical tissue sealant.

In one embodiment of the surgical instrument that is adapted to deliver surgical fasteners, the surgical instrument further comprises at least one energy module that includes at least one of a battery, a capacitor, a fuel cell, a mechanical energy storage device, or a fluid energy storage device. The force is generated from the delivery mechanism may include at least one of a pressurized gas canister/cartridge, a spring, a lever, an explosive charge, a piezoelectric actuator, an electric motor, an electroactive polymer or a solenoid. In a further variant of the embodiment, at least one energy module is located within or in a proximity to at least one grasping jaw. Moreover, at least one energy module may be located outside at least one grasping jaw but within a portion of the surgical instrument. Additionally, in some embodiments at least one energy module may be located outside at least one grasping jaw. At least one energy module may transmit energy through a medium containing at least one of a wire, a tube, an optical fiber or a waveguide. Alternatively, at least one energy module may transmit energy through a wireless device.

In an embodiment of the surgical instrument that is adapted to deliver surgical fasteners, the surgical instrument may include at least one shape-transforming material that contains a shape memory alloy. The shape memory alloy may include at least one of titanium, nickel, zinc, copper, aluminum, cadmium, platinum, iron, manganese, cobalt, gallium or tungsten. In one embodiment, the shape memory alloy may include Nitinol™ or electro-active polymer. In another embodiment, at least one shape-transforming material includes at least one mechanically reconfigurable material.

In one embodiment of the surgical instrument that is adapted to deliver surgical fasteners, the surgical instrument further comprises at least one sensor. The at least one sensor may be disposed within at least one grasping jaw. Furthermore, at least one sensor may be disposed in a proximity to at least one grasping jaw. In one embodiment, at least one sensor includes an image-acquisition device. Furthermore, the image-acquisition device may include at least one of a camera, a charge coupled device, an X-ray receiver, an acoustic energy receiver, an electromagnetic energy receiver or an imaging device. In one embodiment, the image-acquisition device may be wirelessly coupled to at least one visual display. In an embodiment, at least one sensor includes an illumination device that is operably coupled to at least one image-acquisition device. In yet another embodiment, at least one sensor includes a data-transmission device.

Furthermore, the surgical instrument adapted to deliver surgical fasteners includes at least one sensor includes a proximity detector, which may be adapted to detect proximity of a biological tissue to the surgical instrument. Furthermore, the proximity detector includes, in one embodiment, an electromagnetic energy emitter or an electromagnetic energy receiver. In other embodiments, the proximity detector includes an acoustic energy emitter and an acoustic energy receiver. The proximity detector may further include a point source emitter or a source illuminator.

An embodiment, the surgical instrument that is adapted to deliver surgical fasteners provides for a point source emitter or a source illuminator that is operably coupled to at least one image acquisition device. In another embodiment, the point source emitter or a source illuminator includes at least one of an ultrasonic source, an acoustic source, a visible source, an ultraviolet source, a gamma ray source, an X-ray source or an infrared source. Here the point source emitter or a source illuminator may be operably configured within a grasping jaw of the surgical instrument. The proximity detector may additionally include a communication medium for communication with at least one image display. In one embodiment, the proximity detector includes at least one image-transmission device. In another embodiment, the proximity detector includes at least one data-transmission device. In yet another embodiment, the proximity detector is wirelessly coupled to at least one image display. In an embodiment, at least one sensor provides a feedback signal, which may be a datum or an image to a human or robotic user. In another embodiment, at least one sensor provides a force feedback signal to a force generator mechanism. Furthermore, at least one sensor may provide a signal, a datum or an image regarding status of the number of staples in the surgical instrument.

In one embodiment, the surgical instrument that is adapted to deliver surgical fasteners, the surgical instrument further comprises at least one cutter. Another embodiment provides at least one cutter is an optical cutter. The optical cutter may include a laser-mediated cutting device. The cutter may include at least one cutter is an electro-thermal cutter in one embodiment. Furthermore, at least one cutter may include one of a blade, a knife or an edge. In another embodiment, at least one cutter is operably coupled to at least one grasping jaw.

In an embodiment, the surgical instrument that is adapted to deliver surgical fasteners includes a chemical tissue sealant is housed inside at least one grasping law. In another embodiment, the chemical tissue sealant is a biocompatible chemical tissue sealant or a biodegradable chemical tissue sealant. In yet another embodiment, the chemical tissue sealant is delivered in a proximity to at least one fastener. One other embodiment provides for a chemical tissue sealant that is delivered between at least two adjacent layers of body tissue.

In some embodiments, the surgical instrument that is adapted to deliver surgical fasteners includes the surgical instrument delivers surgical fasteners that include staples, pins or ties. The surgical instrument may have at least one grasping jaw that has a curvature that conforms to a body tissue. Furthermore, more than two grasping jaws may be included in the surgical instrument.

Moreover, the surgical instrument that is adapted to deliver surgical fasteners may comprise a flexually deformable and steerable shaft connected to at least one grasping jaw, and may contain at least one shape-transforming material. In some embodiments, the at least one shape-transforming material contains a shape memory alloy. The shape memory alloy may include at least one of titanium, nickel, zinc, copper, aluminum, cadmium, platinum, iron, manganese, cobalt, gallium or tungsten. In some embodiments, the shape memory alloy includes Nitinol™ or electro-active polymer. In an embodiment, the shape-transforming material includes at least one mechanically reconfigurable material.

In one aspect, an embodiment of the surgical instrument comprises at least one grasping jaw or at least one delivery mechanism adapted to deliver surgical fasteners. The delivery mechanism being located in a proximity to or is contained within at least one grasping jaw. In some embodiments, the surgical fasteners contain at least one shape-transforming material or at least one cutter. At least one grasping jaw is configured to movably operate in an opposing manner with respect to at least one other grasping jaw. In another embodiment, at least one grasping jaw is configured to operably mate with at least one other grasping jaw. Furthermore, at least one grasping jaw is configured to serve as an anvil for forming an interaction surface between at least one surgical fastener and bodily tissues, the forming being facilitated by reversible mating and unmating of the anvil with an opposite grasping jaw. In an embodiment, at least one grasping jaw forms an annular grasp around a body tissue.

The following embodiments are directed to a surgical instrument that is adapted to deliver surgical fasteners and may contain at least one shape-transforming material or at least one cutter.

One embodiment of the surgical instrument adapted to deliver surgical fasteners provides that a delivery mechanism utilizes a force generated from the delivery mechanism contained within or in a proximity to at least one grasping jaw. Another provides that the delivery mechanism results in delivery of one or more linear rows of surgical fasteners. Furthermore, the force is generated from the delivery mechanism that includes at least one of a pressurized gas canister/cartridge, a spring, a lever, an explosive charge, a piezoelectric actuator, an electric motor, an electroactive polymer or a solenoid.

The surgical instrument that is adapted to deliver surgical fasteners further comprises at least one energy module that includes at least one of a battery, a capacitor, a fuel cell, a mechanical energy storage device, or a fluid energy storage device. In an embodiment, at least one energy module is located within or in a proximity to at least one grasping jaw.

Yet another embodiment the surgical instrument that is adapted to deliver surgical fasteners includes at least one energy module that is located outside at least one grasping jaw but within a portion of the surgical instrument. Furthermore, at least one energy module may be located outside at least one grasping jaw. In addition, at least one energy module may transmit energy through a medium containing at least one of a wire, a tube, an optical fiber or a waveguide. Alternatively, at least one energy module transmits energy through a wireless device.

In an embodiment of the surgical instrument that is adapted to deliver surgical fasteners, at least one surgical fastener contains one shape-transforming material, which may include a shape memory alloy. The shape memory alloy may further include at least one of titanium, nickel, zinc, copper, aluminum, cadmium, platinum, iron, manganese, cobalt, gallium or tungsten. Alternatively, shape memory alloy includes Nitinol™ or electro-active polymer. An embodiment may have at least one shape-transforming material that includes at least one mechanically reconfigurable material.

In an embodiment, the surgical instrument that is adapted to deliver surgical fasteners further comprises at least one sensor. In another embodiment, at least one sensor is disposed within at least one grasping jaw. Yet another embodiment may include at least one sensor that is disposed in a proximity to at least one grasping jaw. Furthermore, at least one sensor may include an image-acquisition device. The image-acquisition device may include at least one of a camera, a charge coupled device, an X-ray receiver, an acoustic energy receiver, an electromagnetic energy receiver or an imaging device. Furthermore, the image-acquisition device may be wirelessly coupled to at least one visual display. The sensor may include an illumination device that is operably coupled to at least one image-acquisition device. In an embodiment, at least one sensor includes a data-transmission device. Furthermore, at least one sensor includes a proximity detector. The proximity detector may be adapted to detect proximity of a biological tissue to the surgical instrument. Furthermore, proximity detector may include an electromagnetic energy emitter or an electromagnetic energy receiver. In another embodiment, the proximity detector includes an acoustic energy emitter and an acoustic energy receiver. The proximity detector may further include a point source emitter or a source illuminator. Additional embodiments may include the point source emitter or a source illuminator being operably coupled to at least one image acquisition device. In another embodiment, the point source emitter or a source illuminator includes at least one of an ultrasonic source, an acoustic source, a visible source, an ultraviolet source, a gamma ray source, an X-ray source or an infrared source. In yet another embodiment, the point source emitter or a source illuminator is operably configured within a grasping jaw. Still another embodiment includes a proximity detector that may communicate through a medium with at least one image display. An embodiment provides that the proximity detector includes a communication medium for communication with at least one image display. Furthermore, the proximity detector includes at least one data-transmission device. In another embodiment, the proximity detector is wirelessly coupled to at least one image display. Yet another embodiment, at least one sensor provides a feedback signal, a datum or an image to a human or robotic user. Still another embodiment provides that at least one sensor communicates a force feedback signal to a force generator mechanism. At least one sensor provides a signal, a datum or an image regarding status of the number of staples in the surgical instrument.

An embodiment, the surgical instrument that is adapted to deliver surgical fasteners has at least one cutter that may be an optical cutter. The optical cutter may be a laser-mediated cutting device. At least one cutter may be an electro-thermal cutter. In another embodiment, least one cutter includes one of a blade, a knife or an edge. In yet another embodiment, at least one cutter is operably coupled to at least one grasping jaw.

In an embodiment, the surgical instrument that is adapted to deliver surgical fasteners further comprises a chemical tissue sealant. The chemical tissue sealant may be housed inside at least one grasping jaw. Another embodiment provides that the chemical tissue sealant is a biocompatible chemical tissue sealant. Further embodiments specify that the chemical tissue sealant is a biodegradable chemical tissue sealant. Still another embodiment provides that the chemical tissue sealant be delivered in a proximity to at least one fastener and is delivered between at least two adjacent layers of body tissue.

In one embodiment, surgical fasteners include staples, pins or ties. The surgical instrument further comprises in an embodiment at least one grasping jaw having a curvature that conforms to a body tissue. Furthermore the surgical instrument comprises more than two grasping jaws. The surgical instrument may further comprise a flexually deformable and steerable shaft connected to at least one grasping jaw. Embodiments of the flexually deformable and steerable shaft may contain at least one shape-transforming material. Furthermore, at least one shape-transforming material contains a shape memory alloy, which may contain at least one of titanium, nickel, zinc, copper, aluminum, cadmium, platinum, iron, manganese, cobalt, gallium or tungsten. The shape memory alloy may include Nitinol™ or electro-active polymer or at least one mechanically reconfigurable material.

A further aspect of a surgical instrument involves a method of splicing body organs/tissues. In an embodiment, the method comprises the steps of grasping a body tissue with at least one grasping jaw; adjusting a configuration of the grasping in response to a signal or a datum or an image; and releasing a surgical staple/fastener in response to the signal, datum or image. In another embodiment, the method includes grasping a body tissue includes performing end-to-end anastomosis, side-to-side anastomosis, individual ligation, endoscopic or laparoscopic gastro-intestinal operations which include at least one of a bronchus, a pulmonary artery, a pulmonary vein, a large or small intestine, a stomach, a blood vessel or skin. The grasping a body tissue may include aligning the body organs between the at least one grasping jaw in a manner compatible with surgical or anastomosis operations. In an embodiment, the grasping operation may include displaying an image of the tissue being grasped. Furthermore, adjusting a configuration of the grasping includes annularly adjusting a grasp around the organs/tissues based on the signal or datum or image. In another embodiment, the releasing of a surgical staple/fastener includes driving a plurality of staple/fasteners into at least one layer of body tissue. In still another embodiment, releasing a surgical staple/fastener includes securing at least one layer of a body tissue with the surgical staple/fastener. In yet another embodiment, releasing a surgical staple/fastener includes deformation of one or more staple/fasteners that undergo a conformational change to close a puncture site. Furthermore, releasing a surgical staple/fastener includes closing at least one or more wound sites. The method may additionally include releasing a surgical staple/fastener and a suitable amount of a chemical tissue sealant that permits wound healing.

An aspect of a surgical instrument includes a method of splicing body organs/tissues comprising: means for grasping a body tissue; means for adjusting a configuration of the grasping in response to a signal or a datum or an image; and means for releasing a surgical staple/fastener in response to the signal, datum or image.

In addition to the foregoing, other system aspects are described in the claims, drawings, and text forming a part of the present disclosure. Furthermore, various other method or system or program product aspects are set forth and described in the teachings such as text (e.g., claims or detailed description) or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
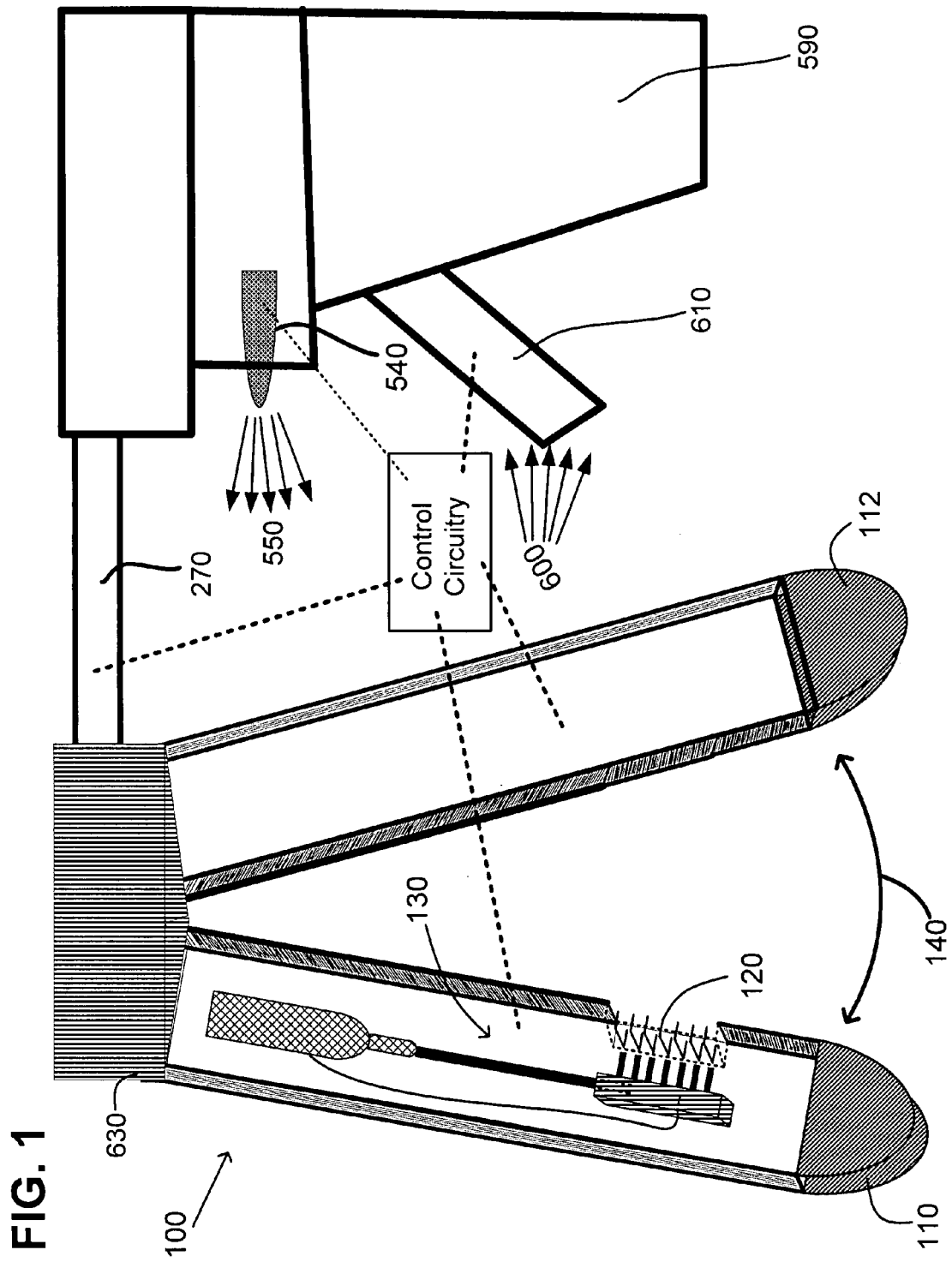
FIG. 1 is a system-level illustration of an exemplary surgical instrument in which embodiments such as grasping jaws and an exemplary force generator mechanism may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The following disclosure is drawn to a surgical instrument. FIG. 1 shows a system-level schematic illustration of an embodiment of the surgical instrument 100 comprising at least one grasping jaw 110, the at least one grasping jaw being adapted to deliver surgical staples 120 by a force generated from a force generator mechanism 130 that is contained within the at least one grasping jaw 110 or is in a proximity to the at least one grasping jaw. The grasping jaws 110, 112 may be movably 140 attached to a hinge 630. At a system level, the surgical instrument further comprises control circuitry that may control one or more parts of the surgical instrument. Additionally, the surgical instrument may optionally include a hinge 630 that connects the jaws. There is included a shaft 270 connecting the jaws or hinge to a handgrip 590. The handgrip includes a trigger 610. The handgrip includes a signal generator 540 that is capable of communicating a signal 550. In some embodiments of the surgical instrument the trigger/handgrip is adapted to receive a feedback signal 600 that may communicate to a user information regarding the functional status of the surgical instrument.

As used herein, the terms "grasping jaws" or "jaws" include, but are not limited to, any of the various parts or whole of a surgical stapler or parts thereof or similar surgical stapling or anastomosis devices. Illustrative examples of such staplers, stapling devices or anastomosis devices may be those suitable for use in any medical or surgical care including performing end-to-end anastomosis, side-to-side anastomosis, individual ligation, endoscopic or laparoscopic gastrointestinal operations. Such operations may involve for example, at least one of a bronchus, a pulmonary artery, a pulmonary vein, a large or small intestine, a stomach, a blood vessel or skin.

Figure 2:
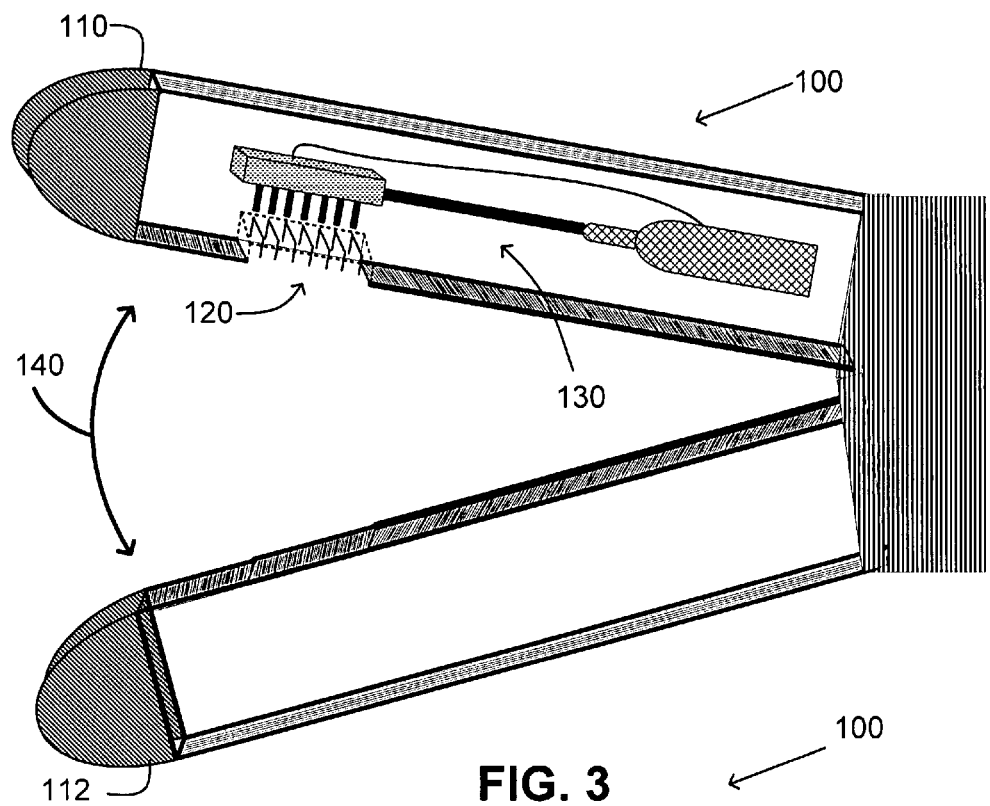
FIG. 2 is a schematic of a surgical instrument that includes an exemplary illustrative embodiment of movable grasping jaws that includes an exemplary illustration of a force generator mechanism.

Turning now to FIG. 2, which is an exemplary illustration of a surgical instrument 100 wherein at least one grasping jaw 110 is configured to movably 140 operate in an opposing manner with respect to at least one other grasping jaw 112.

Figure 3:
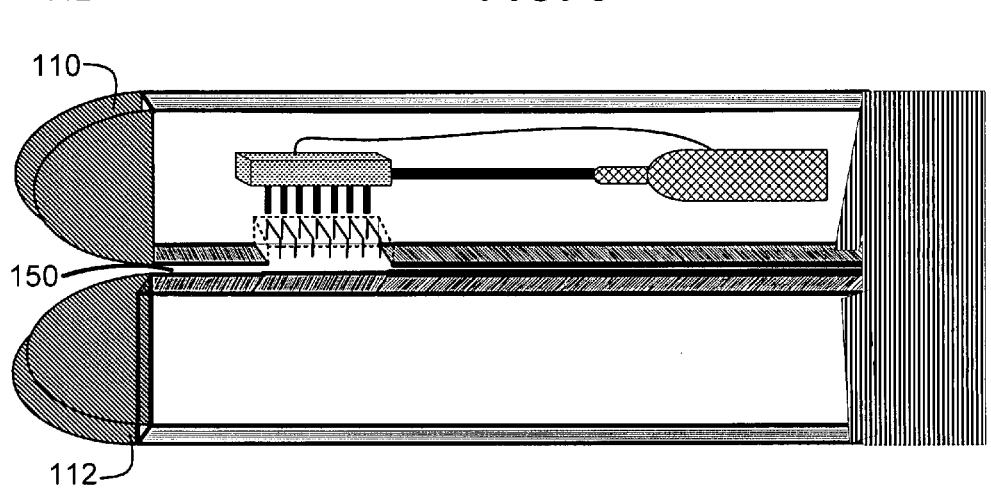
FIG. 3 is a schematic of a surgical instrument that includes an exemplary illustrative embodiment of closed mating position of movable grasping jaws that includes an exemplary illustration of a force generator mechanism.

FIG. 3 illustrates an exemplary surgical instrument 100 showing an embodiment of at least one grasping jaw 110 that is configured to operably mate 150 with at least one other grasping jaw 112. The term "mate" includes, but is not limited to, juxtapositioning, "coming together" or aligning any or all parts of each grasping jaw. Mating includes, but is not limited to, complete or partial coupling of the grasping of the jaws.

Figure 4:
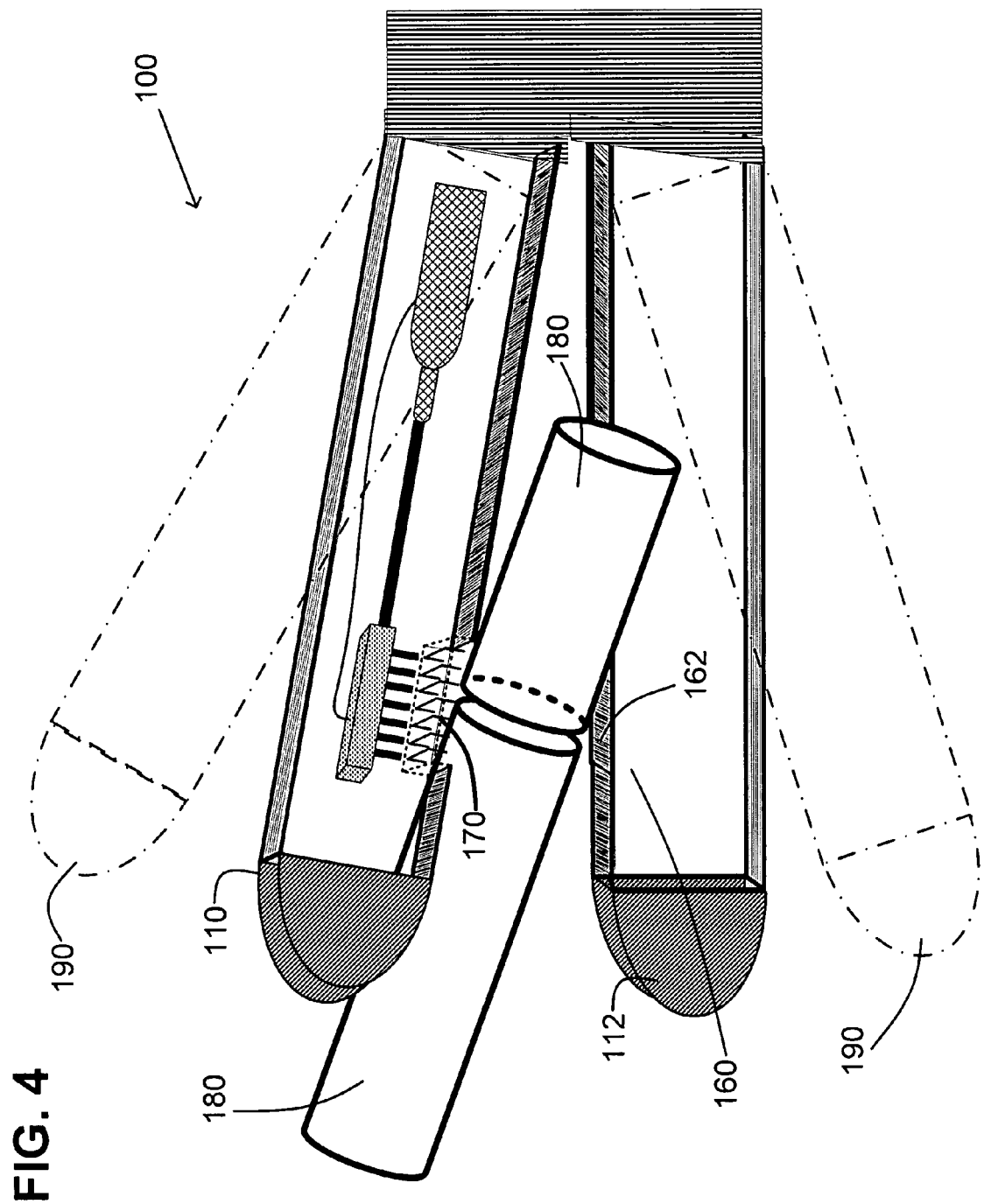
FIG. 4 is a schematic of a surgical instrument that includes an illustrative example of mating grasping jaws configured to grasp tubular organs/tissues.

As illustrated in FIG. 4, at least one grasping jaw 112 is configured to serve as an anvil 160 for forming an interaction surface 162 between at least one surgical staple 170 and bodily tissues 180, the forming being facilitated by reversible mating and unmating 190 of the anvil with an opposite grasping jaw 112. Those skilled in the art will recognize that mating and unmating of the grasping jaws may be limited to the movement of at least one grasping jaw while the other grasping jaw may be stationary. Furthermore, the illustration in FIG. 4 does not necessarily limit the surgical instrument to only two jaws. One skilled in the art may envisage similar surgical instruments with more than two grasping jaws that are aligned to achieve the same or similar results illustrated in FIG. 4.

Figure 5:
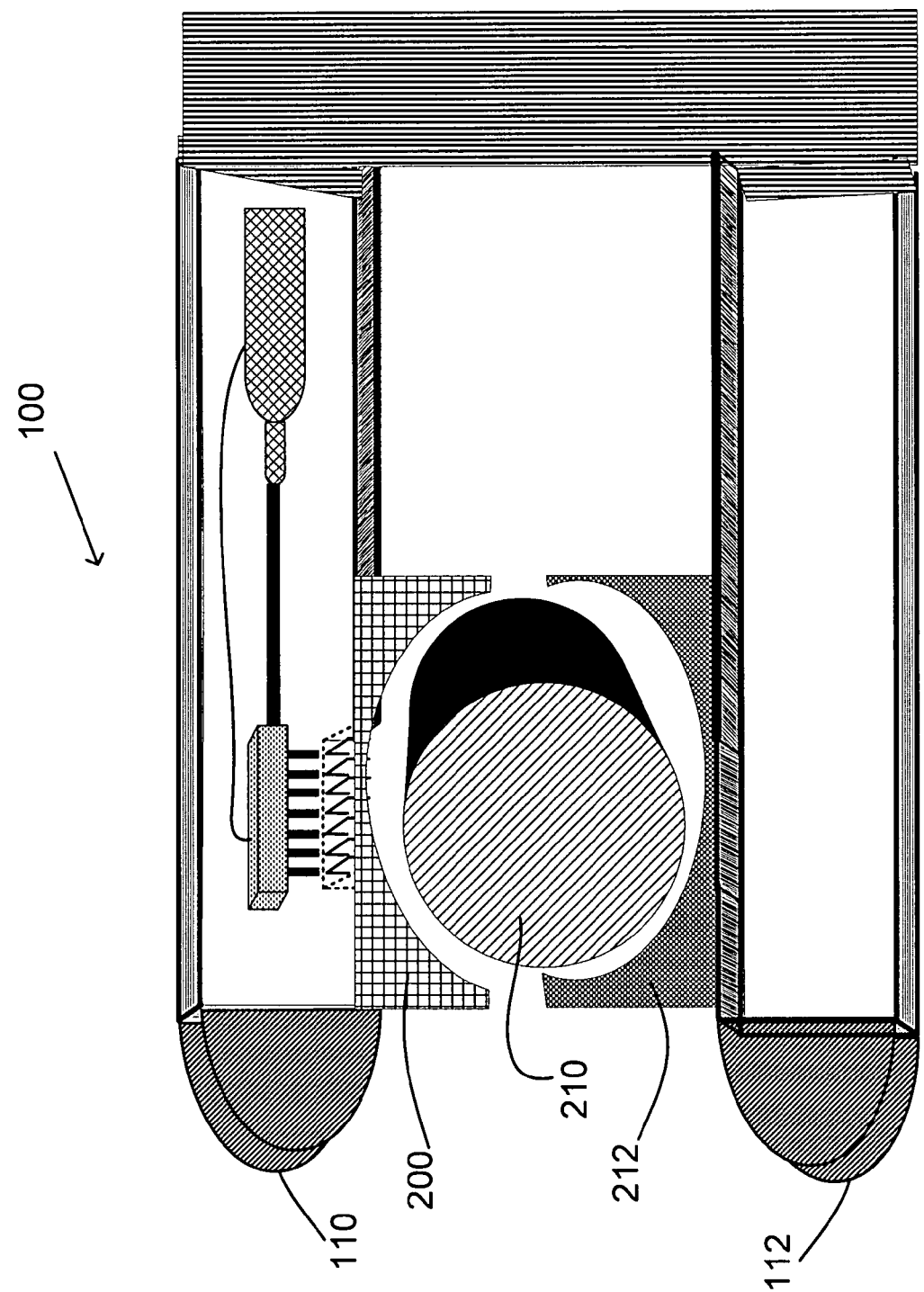
FIG. 5 is a schematic of a surgical instrument including an exemplary illustration of two grasping jaws adapted to provide an annular grasp around an exemplary illustration of a bodily organ.

FIG. 5 shows an exemplary embodiment of a surgical instrument 100 illustrating at least one grasping jaw 110 that forms an annular grasp 200 around a body tissue 210. In another embodiment, the other grasping jaw 112 may form a complementary annular grasp 212. Those skilled in the art will realize that the grasping jaws may be configured to alter the shape and size of the grasping surface based on the size and shape of the bodily organs or tissues. In other words, grasping jaws may be constructed in different sizes and shapes to fit the various bodily organs and tissues of patients. Furthermore, one or more grasping jaws may be configured to enter the lumen of tubular organs during anastomosis procedures.

In an embodiment, the terms "bodily", "body" or "patient" refer to a human or any animal including domestic, marine, research, zoo, farm animals, fowl and sports animals, or pet animals, such as dogs, cats, cattle, horses, sheep, pigs, goats, rabbits, chickens, birds, fish, amphibian and reptile.

In an embodiment, the terms "tissue(s)" or "organs" includes any part of a human or animal body. Examples may include but is not limited to, organs associated with the alimentary canal/digestive tract, pulmonary tract, blood vessels, lumen-containing organs, bones, etc.

Figure 6:
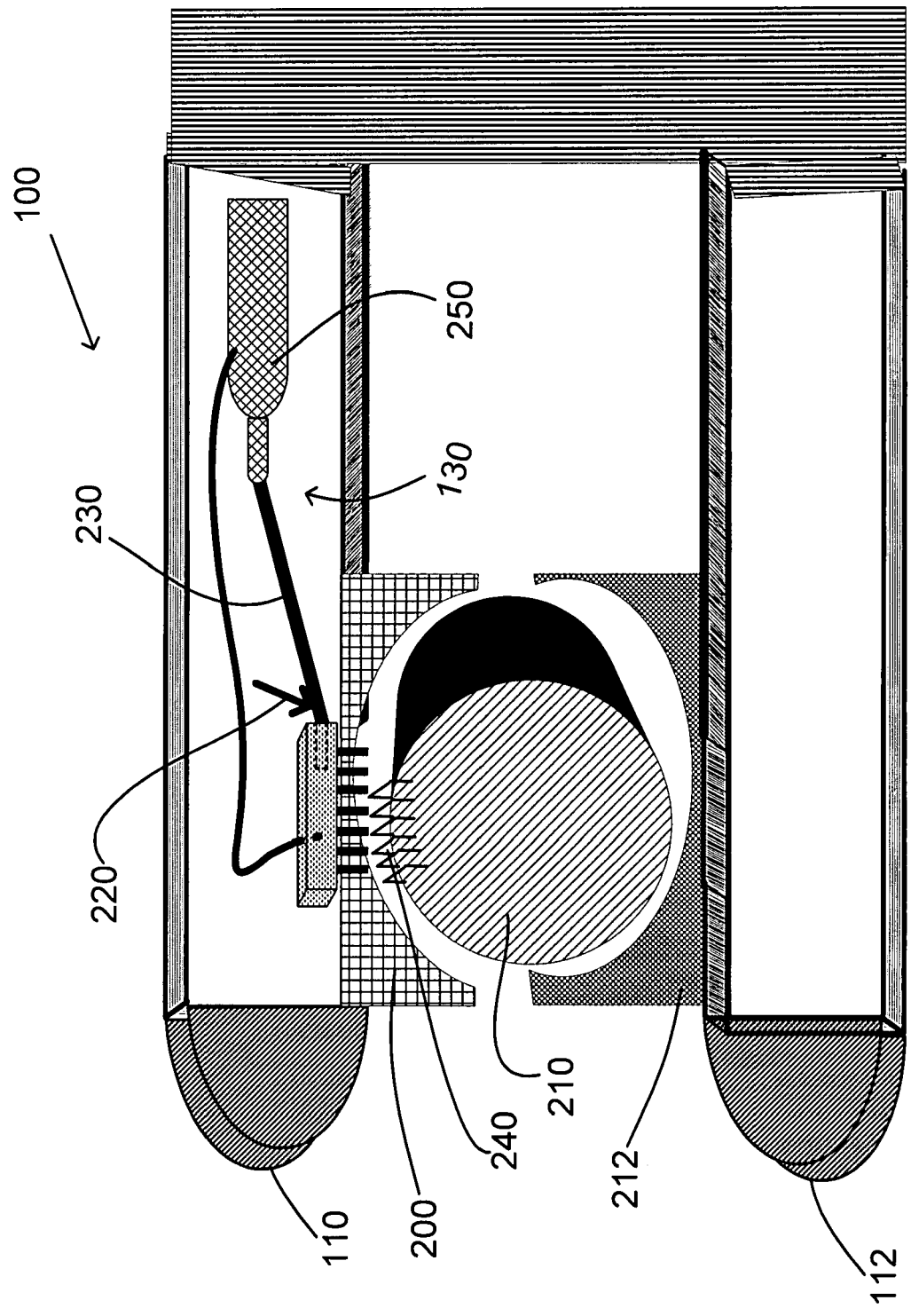
FIG. 6 is a schematic of a surgical instrument including an exemplary illustration of a force generator mechanism that is configured to deliver an exemplary illustration of a linear row of staples into an exemplary illustration of a bodily tissue.

Looking at FIG. 6, in an embodiment of a surgical instrument 100, a force 220 generated from a force generator mechanism 130 is communicated to a medium 230 resulting in the release of one or more linear rows 240 of surgical staples. The force may be generated by a variety of means. In an embodiment, such means may include but are not limited to, an energy module 250. The energy module may include at least one of a battery, a capacitor, a fuel cell, a mechanical energy storage device, or a fluid energy storage device. In another embodiment, the force may be generated through the use of a number of devices, which may include but are not limited to at least one of a pressurized gas canister/cartridge, a spring, a lever, an explosive charge, a piezoelectric actuator, an electric motor, an electroactive polymer or a solenoid.

Figure 7:
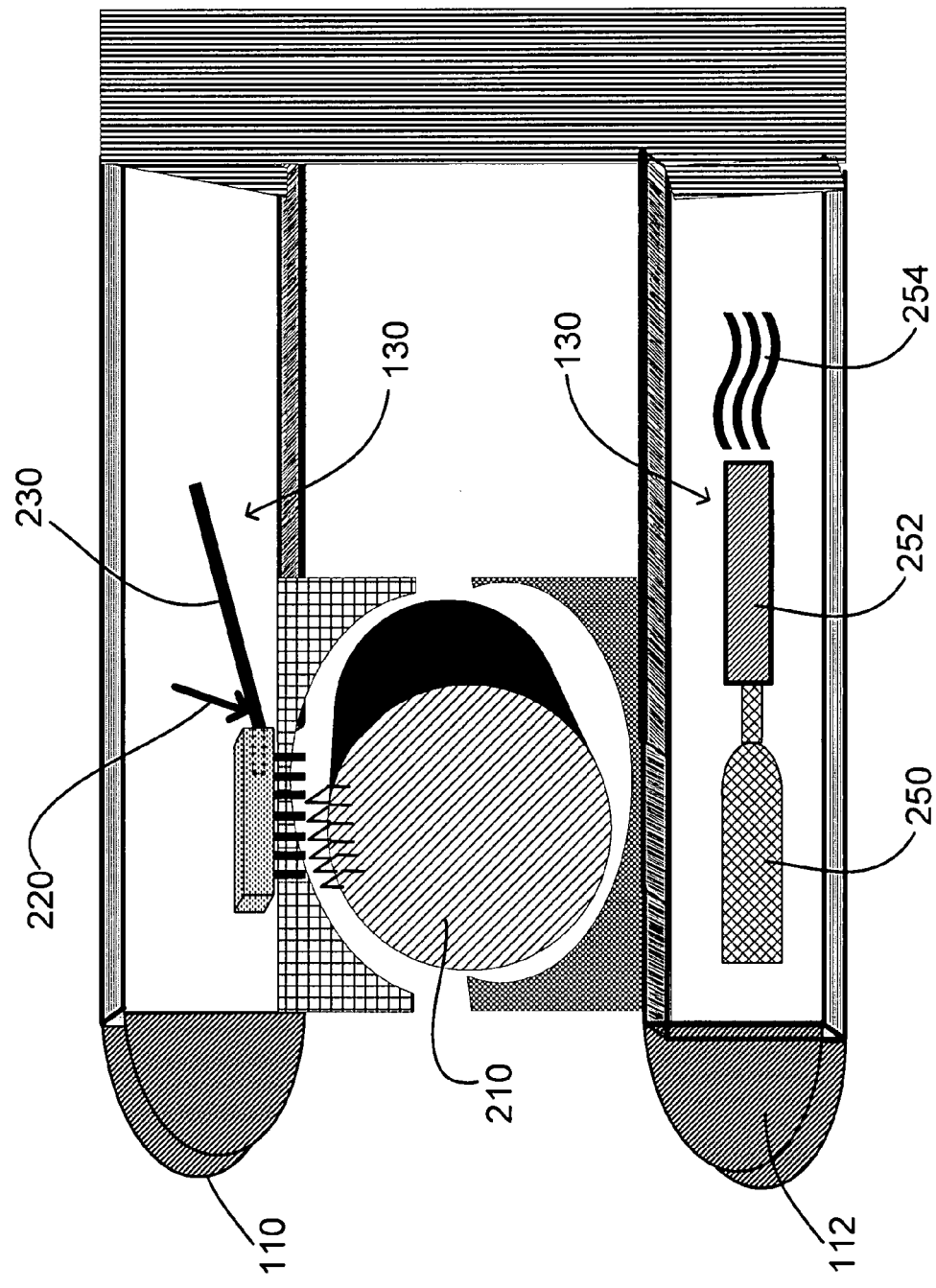
FIG. 7 is a schematic of a surgical instrument that includes an exemplary illustration of a split force generator mechanism located in both illustrative grasping jaws.

In an embodiment, as illustratively exemplified in FIG. 7, at least one energy module 250 may be located within the opposing grasping jaw 112 (or in a proximity to it). Furthermore, the energy module transmits energy 254 through a wireless device 252 to the remotely located force generator mechanism 130. In alternative embodiments, the energy module may transmit energy via a medium that includes but is not limited to at least one of a wire, a tube, an optical fiber or a waveguide.

Figure 8:
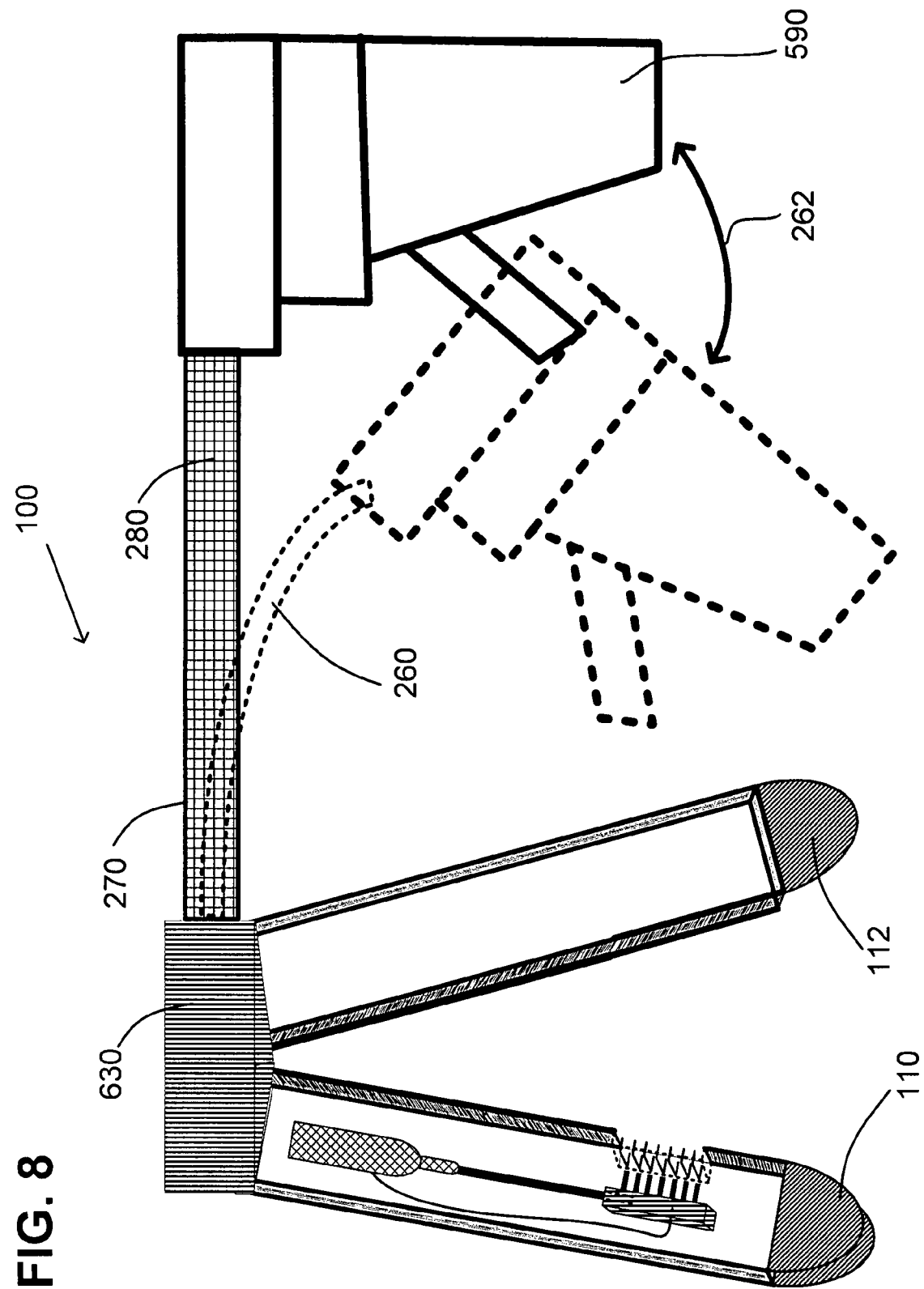
FIG. 8 is a schematic of a surgical instrument that includes an exemplary illustration of an example of a flexually deformable and steerable shaft.

FIG. 8 illustrates a further variation of an exemplary surgical instrument 100. Here, an embodiment further illustrates two grasping jaws 110, 112 that are connected to a flexually deformable and steerable shaft 270 that is connected to the grasping jaw. In an embodiment, the shaft may be connected to the jaws via a hinge 630. In another embodiment, the flexually deformable and steerable shaft contains at least one shape-transforming material 280, which may permit complete or partial deformation 260 of the shaft. Deformation of the shaft may increase the capability of the surgical instrument because the human user may move 262 the handgrip 590 of the surgical instrument in numerous directions, thus enabling the use of the surgical instrument in hard-to-reach areas of the patient's body and around anatomical corners. The shape-transforming material may contain a shape memory alloy or other materials responsive to an input to change shape or physical dimension or characteristic. Examples of shape memory alloy include, but are not limited to, Nitinol™. In addition, embodiments may include at least one of titanium, nickel, zinc, copper, aluminum, cadmium, platinum, iron, manganese, cobalt, gallium or tungsten. Some materials may contain electro-active polymers or mechanically reconfigurable material.

Figure 9:
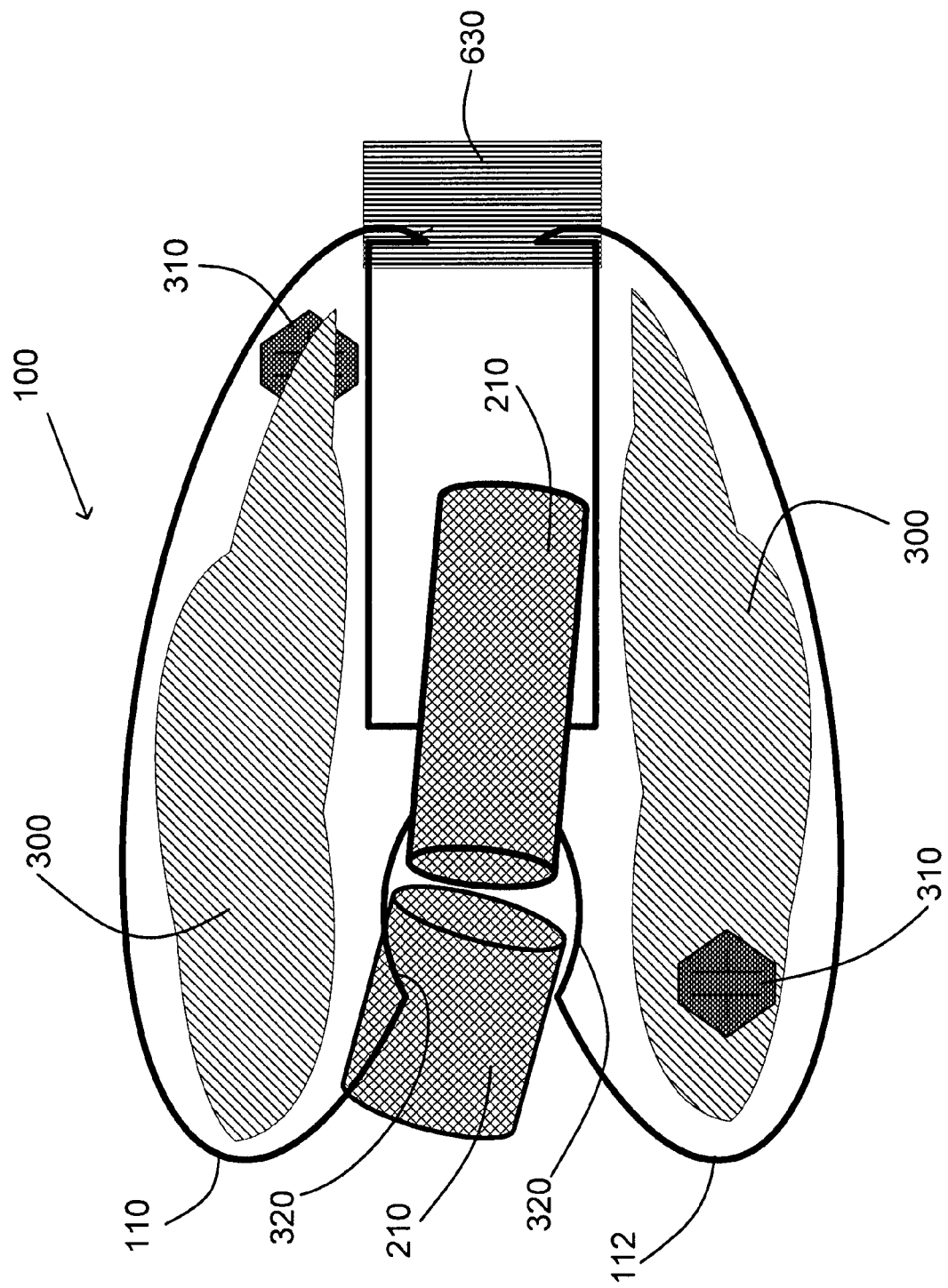
FIG. 9 is a schematic of a surgical instrument including exemplary illustration of shape-conforming grasping jaws with exemplary sensors.

Turning now to FIG. 9, which illustrates an embodiment of a pair of grasping jaws 110, 112. In this example, the grasping jaws may be shaped differently from those exemplified in the above figures and may be further adapted to conform to a shape 320 of a body organ or tissue 210. Conformity may be achieved, inter alia, through the use of shape transforming material 300 provided within the whole or part of the grasping jaws. The shape-transforming material may be distributed in either or both grasping jaws. In an embodiment, at least one sensor 310 may be disposed in one or more of the grasping jaws.

Figure 10:
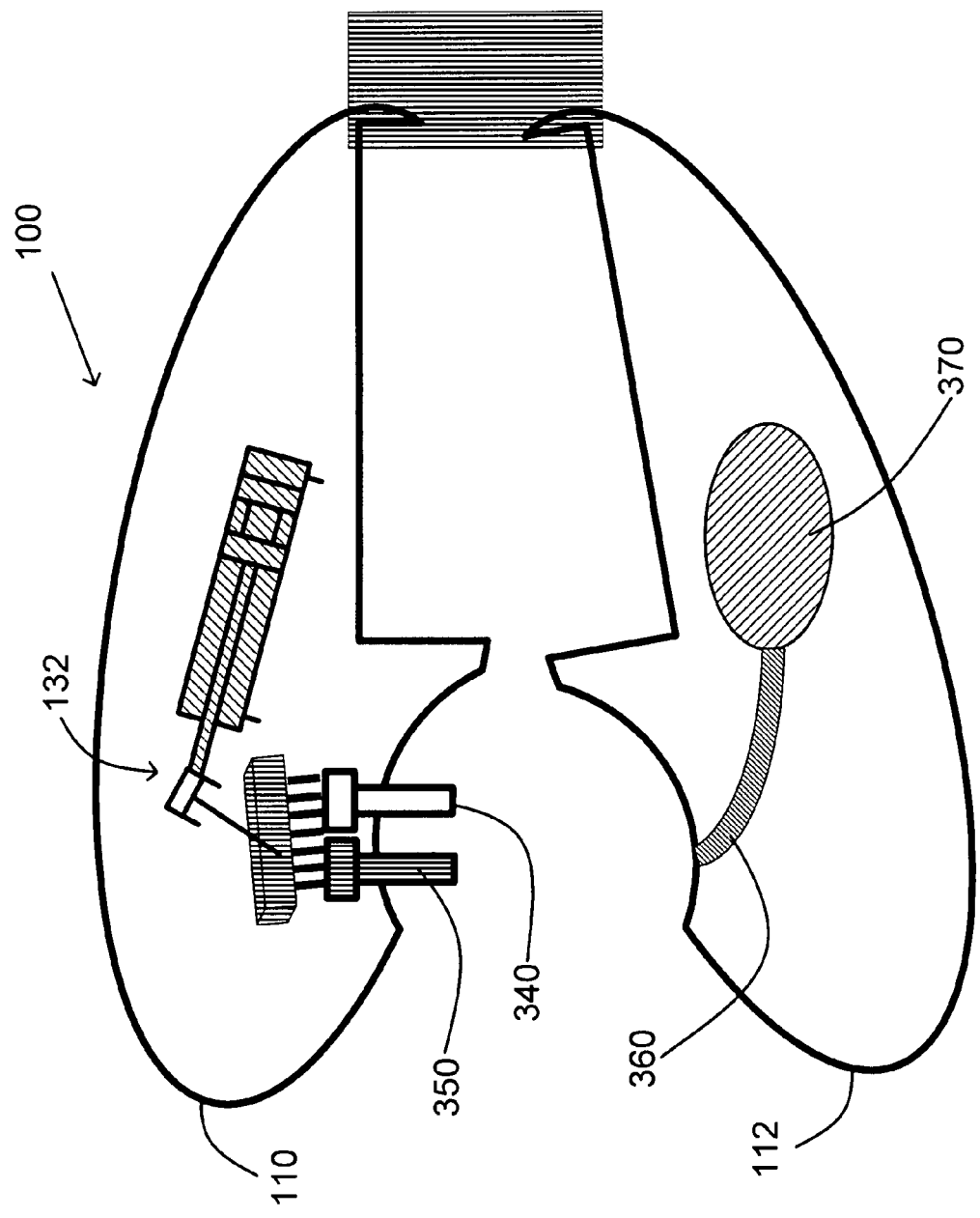
FIG. 10 is a schematic of a surgical instrument including an exemplary illustration of a grasping jaw housing a delivery mechanism for delivering an exemplary fasteners and an illustrative example of a chemical tissue sealant.

In an embodiment of a surgical instrument 100, as illustrated in FIG. 10, at least one grasping jaw 110 and at least one delivery mechanism 132 are adapted to deliver exemplary surgical fasteners 340, 350. Moreover in another embodiment, the delivery mechanism may be contained within at least one grasping jaw 110. Alternatively, the delivery mechanism may be in proximity to a grasping jaw but not within it. Here, the location may include, but is not limited to, another grasping jaw or another portion of the surgical instrument. In yet another embodiment, the surgical fasteners may contain at least one shape-transforming material 350. In still another embodiment, at least one grasping jaw 112 may provide at least one chemical tissue sealant 360. The tissue sealant may be housed in a reservoir 370.

Figure 11:
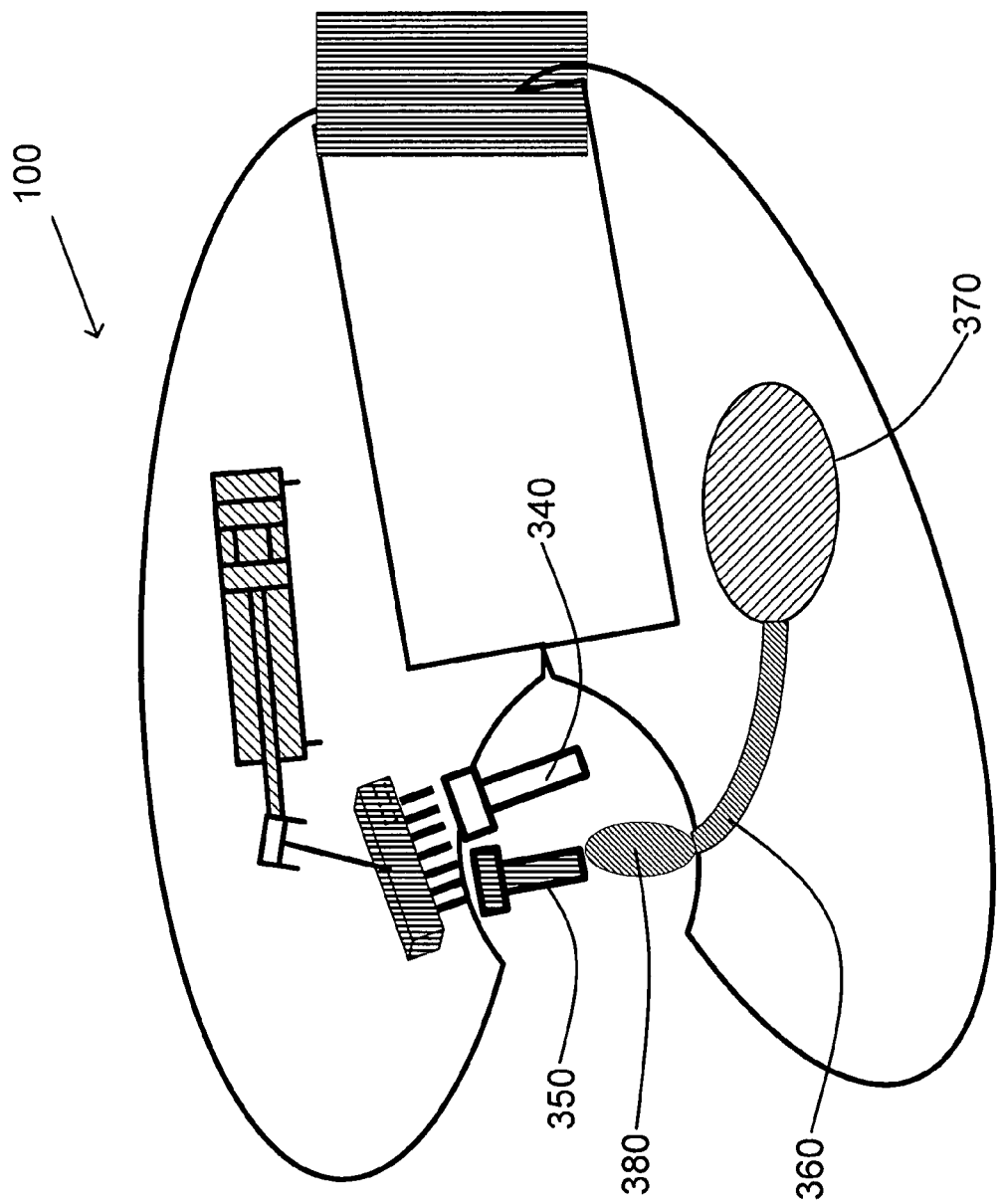
FIG. 11 is a schematic of a surgical instrument including an exemplary illustration of a portion of a chemical tissue sealant deposited in proximity to an exemplary row of surgical fasteners.

FIG. 11 illustrates an embodiment of a surgical instrument 100, in which a portion 380 of the chemical tissue sealant 360 is delivered in a proximity to illustrative surgical fasteners 340. The sealant may be applied prior to or after the deployment of the surgical fasteners 340,350. Here, a portion of the chemical tissue sealant, includes, but is not limited to a drop(s) or droplets or spray or liquid or solid or semi-solid. Further embodiments include the delivery of the chemical tissue sealant in proximity to released fasteners 340, 350.

Figure 12:
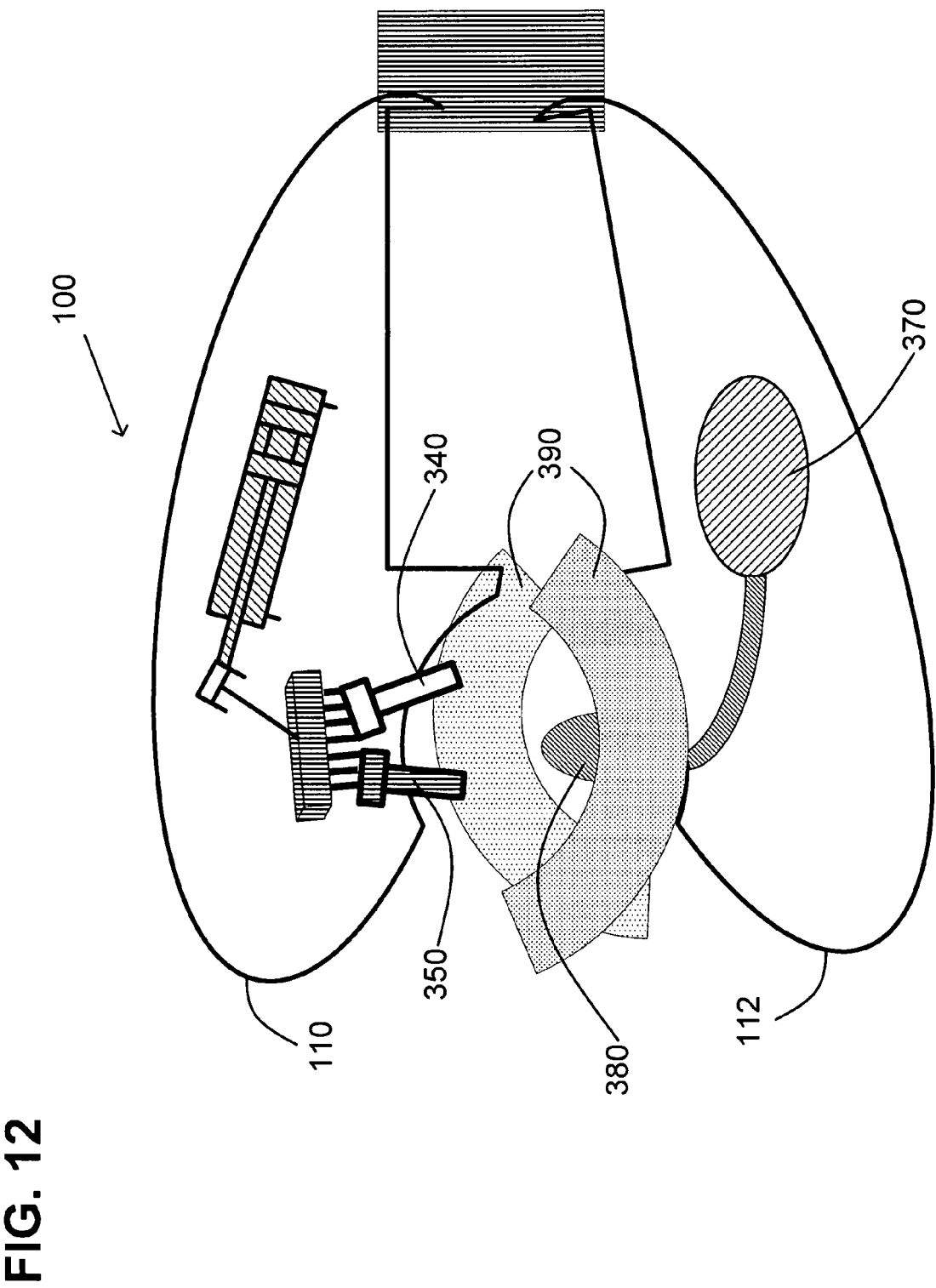
FIG. 12 is a schematic of a surgical instrument including an exemplary illustration of a portion of a chemical tissue sealant deposited in proximity to an exemplary illustration of layers of bodily tissues.

FIG. 12 illustrates that, in an embodiment, the chemical tissue sealant portion 380 may be delivered between at least two adjacent layers 390 of body tissue. Those skilled in the art are aware that here "adjacent layers" includes, and is not limited to, tissue or organs brought together in close proximity to each other during anastomosis operations. The organs or tissues may lie on top of each other or within each other or on a side by side position with respect to each other or in any other position with respect to each other. As used here, the term "layers" includes monolayers, bilayers, multilayers, a single layer, and includes one or more layers of body tissue.

Figure 13:
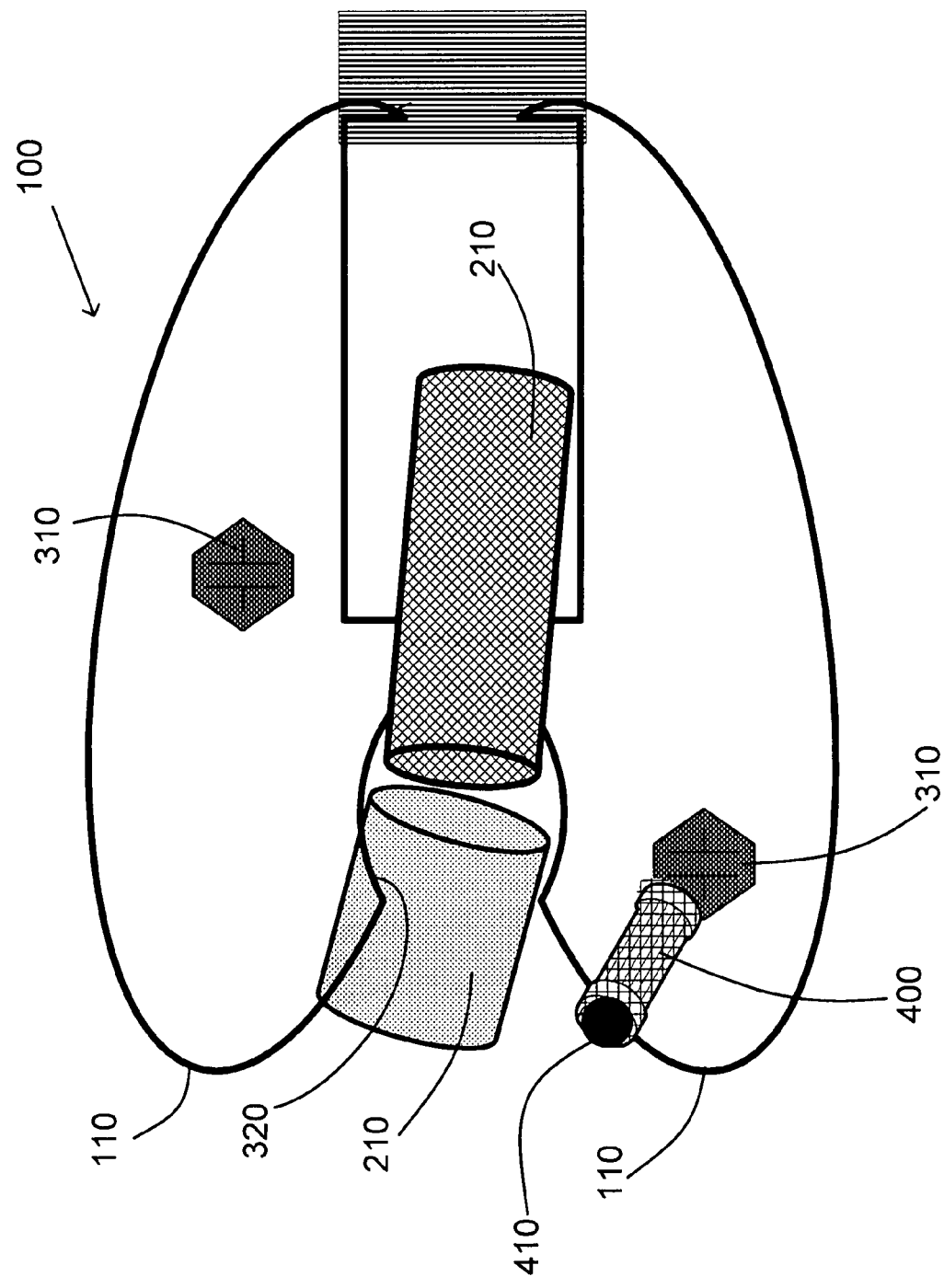
FIG. 13 is a schematic of a surgical instrument including an exemplary illustration of a sensor includes an exemplary illustration of an image acquisition device.

FIG. 13 shows an embodiment of a surgical instrument 100 having two grasping jaws 110, 112 configured to grasp bodily tissues/organs 210. This exemplary illustration further shows at least one grasping jaw 110 that includes at least one sensor 310. In a further embodiment, the other grasping jaw 112 is illustratively shown to carry a sensor 310 as well. In another embodiment, at least one sensor includes an image-acquisition device 400. In yet another embodiment, image-acquisition device includes at least one imaging device 410, which may include but is not limited to one of a lens, a camera, a charge coupled device, an X-ray receiver, an acoustic energy receiver, an electromagnetic energy receiver.

Figure 14:
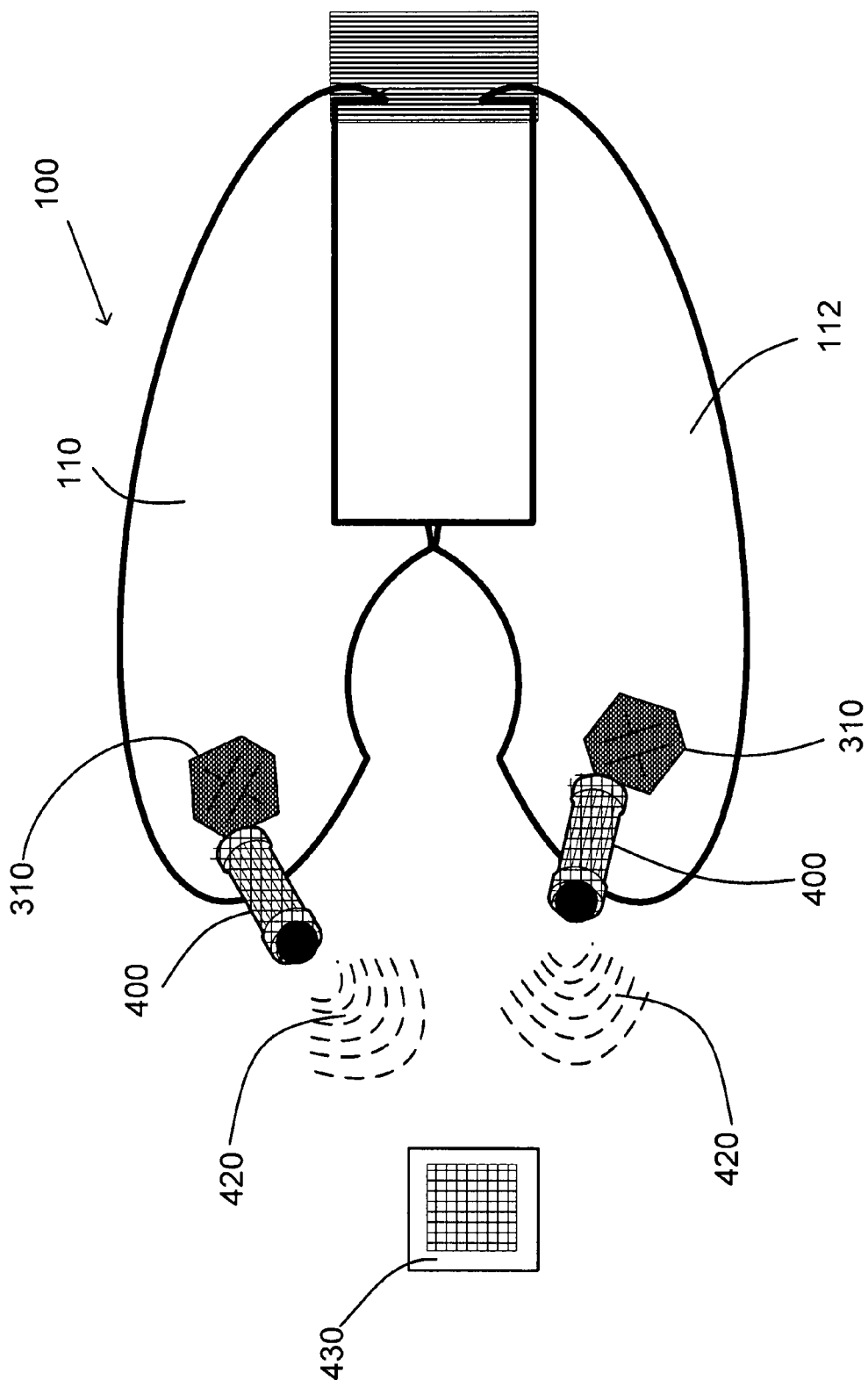
FIG. 14 is a schematic of a surgical instrument including a pair of grasping jaws includes an exemplary illustration of sensors with exemplary illustrations of image acquisition devices in communication with at least one image display.

In still another embodiment, as illustrated in FIG. 14, a surgical instrument 100 may include one or more sensors 310 and image acquisition devices 400. The image acquisition devices may transmit images via a wireless communication medium 420 that is operably coupled with at least one image display 430. The communication medium may include, inter alia, hardwire and at least one image-transmission devices. In an embodiment the image transmission devices may be built into the hardware in the image acquisition devices. Those skilled in the art will recognize that image transmission devices may include those devices which may be used for transmitting encoded data obtained by encoding the data of an image. Examples of image transmission devices are given, for instance, in U.S. Pat. No. 5,305,116 and U.S. Pat. No. 6,157,675, both of which are incorporated herein by reference.

Figure 15:
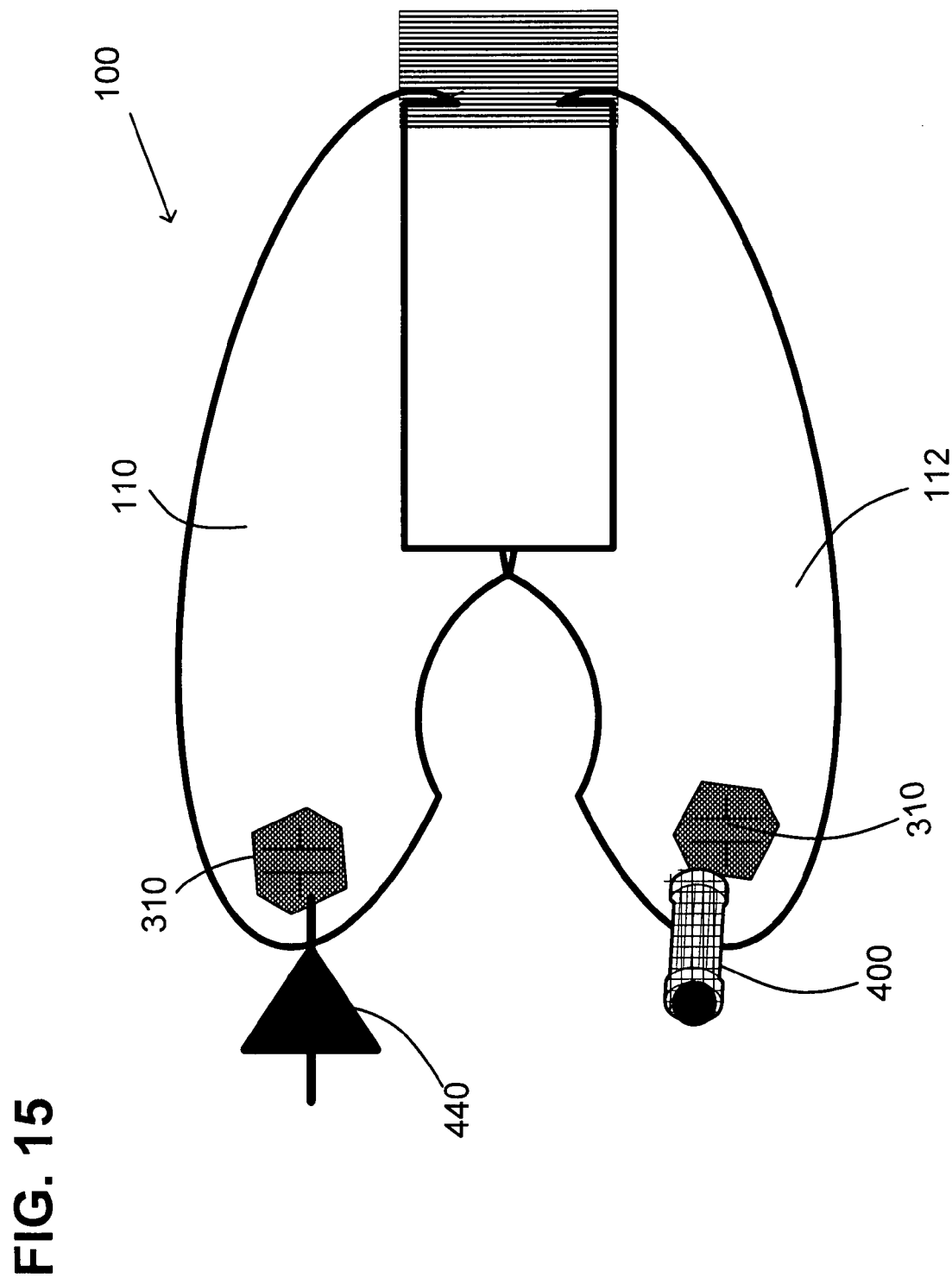
FIG. 15 is a schematic of a surgical instrument including exemplary illustrations of sensors including exemplary an illustration of an image acquisition device and an exemplary illustration of a data-transmission device.

FIG. 15 illustrates at least one sensor 310 that includes a data-transmission device 440. In another embodiment, the surgical instrument 100 may include two grasping jaws 110, 112 that may have two separate sensors 310 each includes either an image acquisition device 400 or a data transmission device 440. Those skilled in the art will realize that some surgical instruments may include more than two grasping jaws containing more than two image acquisition devices or data acquisition devices.

Figure 16:
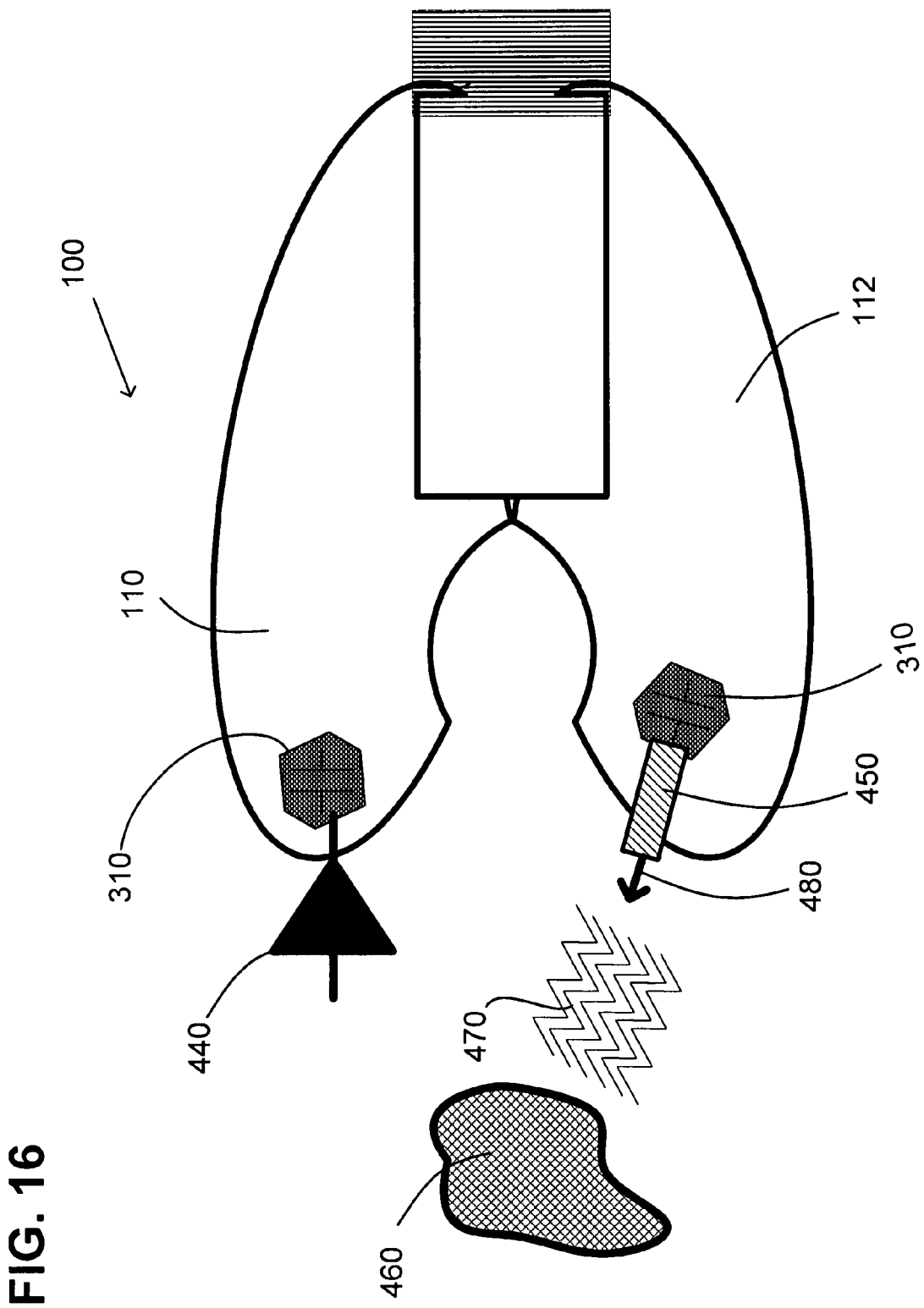
FIG. 16 is a schematic of a surgical instrument including an exemplary illustration of a proximity detector.

Turning to FIG. 16, there is illustrated an embodiment of a surgical instrument 100 that includes at least one grasping jaw 112 that includes a sensor 310 which in turn may include a proximity detector 450. In an embodiment, the proximity detector is adapted to detect proximity of a biological tissue 460 to the surgical instrument 100. In another embodiment, the proximity detector includes an electromagnetic energy emitter or an electromagnetic energy receiver. In yet another embodiment, the proximity detector includes a point source emitter 480 or a source illuminator. In still another embodiment, the point source emitter or a source illuminator emits electromagnetic or acoustic energy 470. The energy emitter includes at least one of an ultrasonic source, an acoustic source, a visible source, an ultraviolet source, a gamma ray source, an X-ray source or an infrared source.

Figure 17:
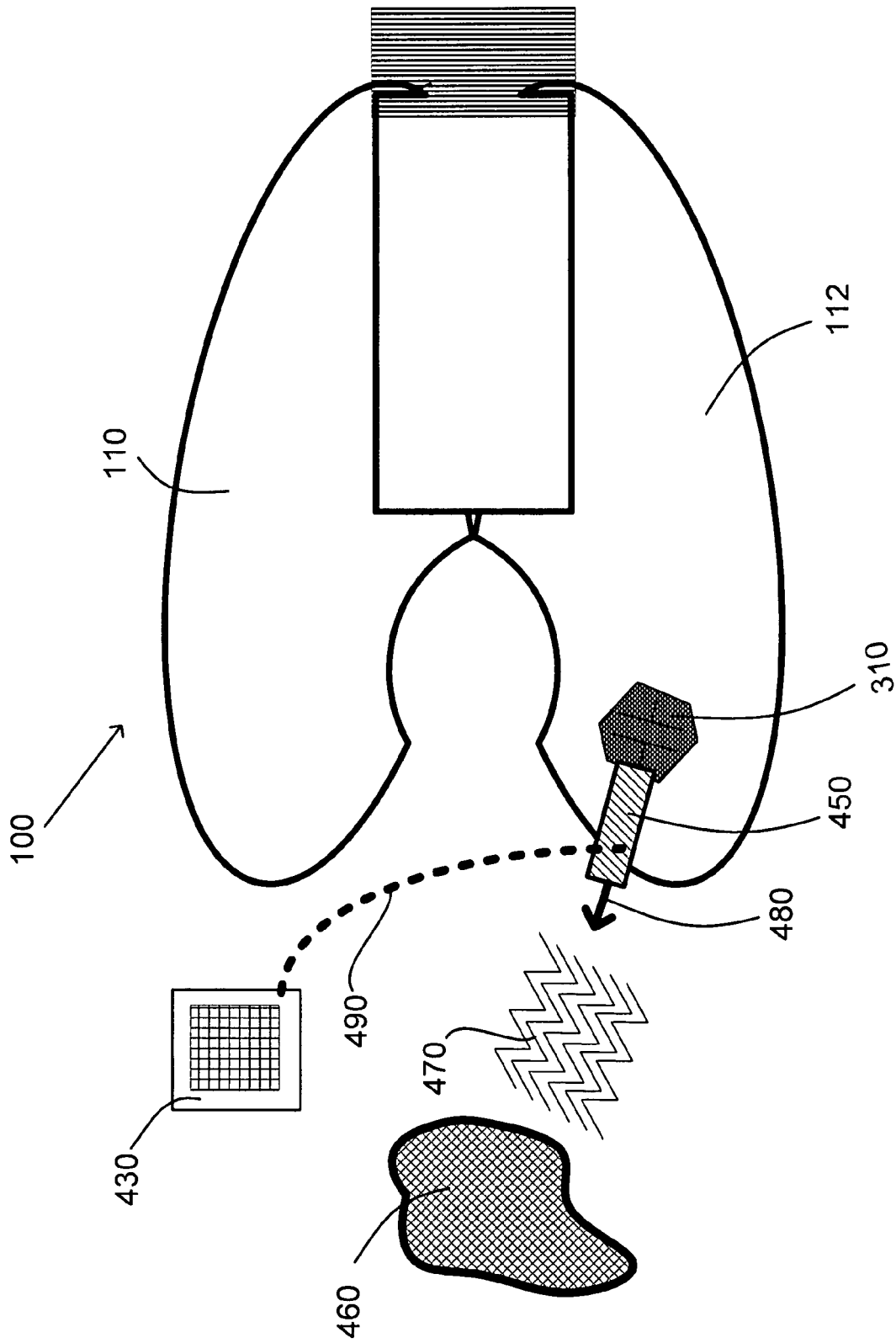
FIG. 17 is a schematic of a surgical instrument including an exemplary illustration of an image acquisition device, an exemplary illustration of a communication medium and an exemplary illustration of a visual display.

FIG. 17 schematically illustrates an exemplary proximity detector 450 that includes a communication medium 490 for communication with at least one image display 430. One skilled in the art will realize that communication includes, but is not limited to, image transmission, data transmission, digital data transmission, analogue data transmission or an audio transmission. One skilled in the art will also recognize that examples of communication media include, but are not limited to the following devices: a wire, a tube, an optical fiber, a waveguide or wireless devices.

Figure 18:
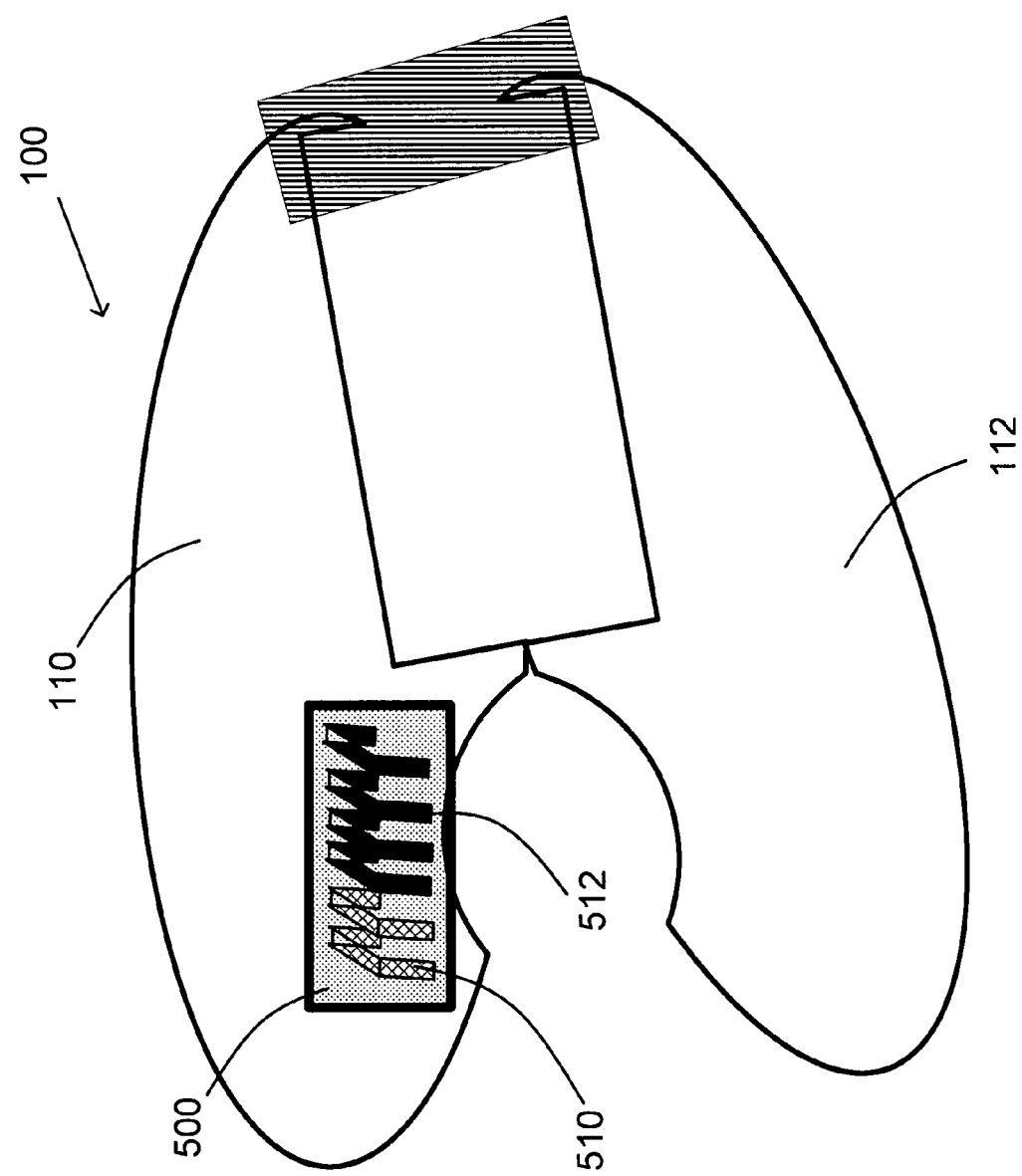
FIG. 18 is a schematic of a surgical instrument including an exemplary illustration of a fastener or staple holder or housing containing an exemplary illustration of an assortment of fasteners/staples.

There is illustrated in an embodiment shown in FIG. 18 a surgical instrument 100 comprising multiple types of surgical fasteners made from an assortment of materials. In an embodiment, one surgical instrument 100 may house 500 exemplary surgical staples made from, for instance, shape transforming material 510 or mechanically reconfigurable material 512. One skilled in the art will recognize that multiple types of surgical fasteners include, but are not limited to surgical fasteners made from different types of materials/compositions, chemical or electrical properties, different shapes and sizes of fasteners, including biocompatible, biodegradable materials. One skilled in the art will further recognize that the above term "house" includes but is not limited to fastener/stapler cartridge holders and the like that are available in the commercial market, and those that are custom-designed and made to fit into surgical stapler-type medical instruments.

Figure 19:
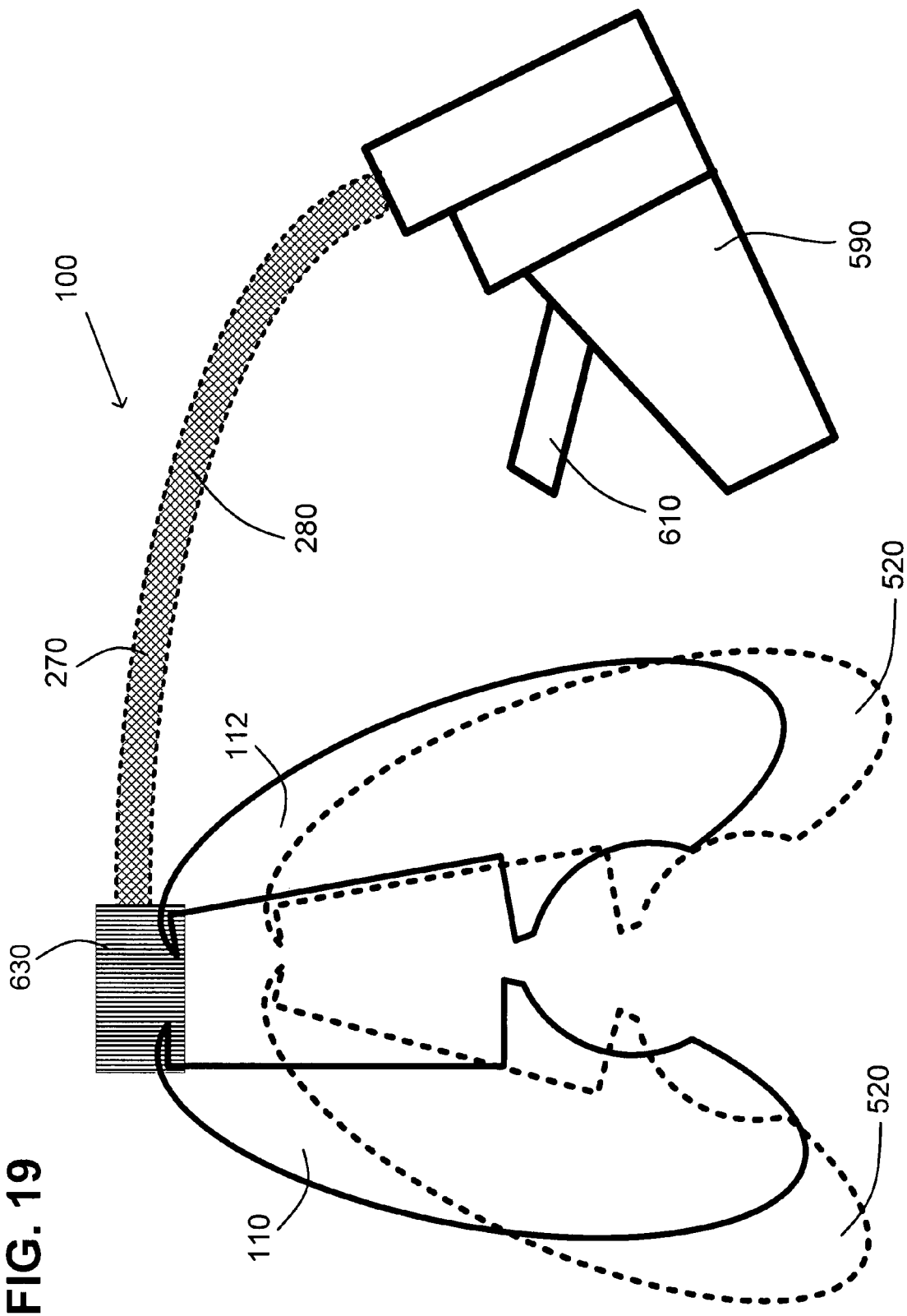
FIG. 19 is a schematic of a surgical instrument including an exemplary illustration of detachable grasping jaws.

In FIG. 19, there is shown an embodiment of a surgical instrument 100 wherein the exemplary grasping jaws 110, 112 are configured to become detachable 520. Those skilled in the art will recognize that detachability of grasping jaws includes, but is not limited to, replacement of used grasping jaws with new ones and disposable grasping jaws. In an embodiment, one or more grasping jaws may be replaced sequentially or simultaneously. Furthermore, detachability of grasping jaws includes, inter alia, replacement grasping jaws of different sizes and shapes or grasping jaws made from different materials/compositions of materials.

Figure 20:
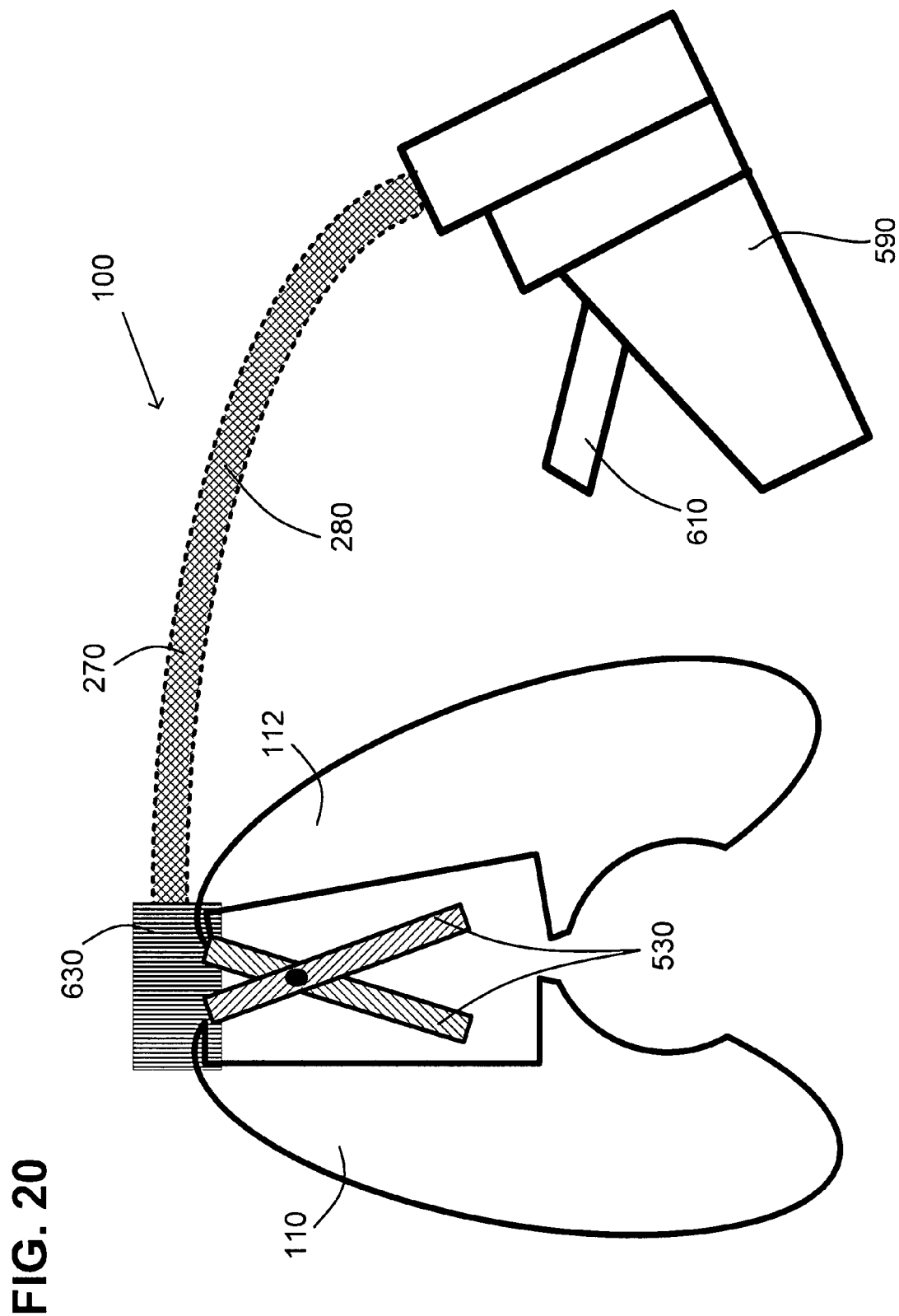
FIG. 20 is a schematic of a surgical instrument including an exemplary illustration of a cutting device.

Turning to FIG. 20, which schematically illustrates an embodiment of a surgical instrument 100 containing an exemplary illustration of a cutting device 530. The surgical instrument may further comprise at least one grasping jaw 110, 112 and a deformable and steerable shaft 270 made from shape transformation material 280. The cutting device may include, but is not limited to, at least one cutter. As recognized by those skilled in the art, cutters may include optical cutters, laser-mediated cutting devices, electro-thermal cutters, a blade, a knife or an edge.

Figure 21:
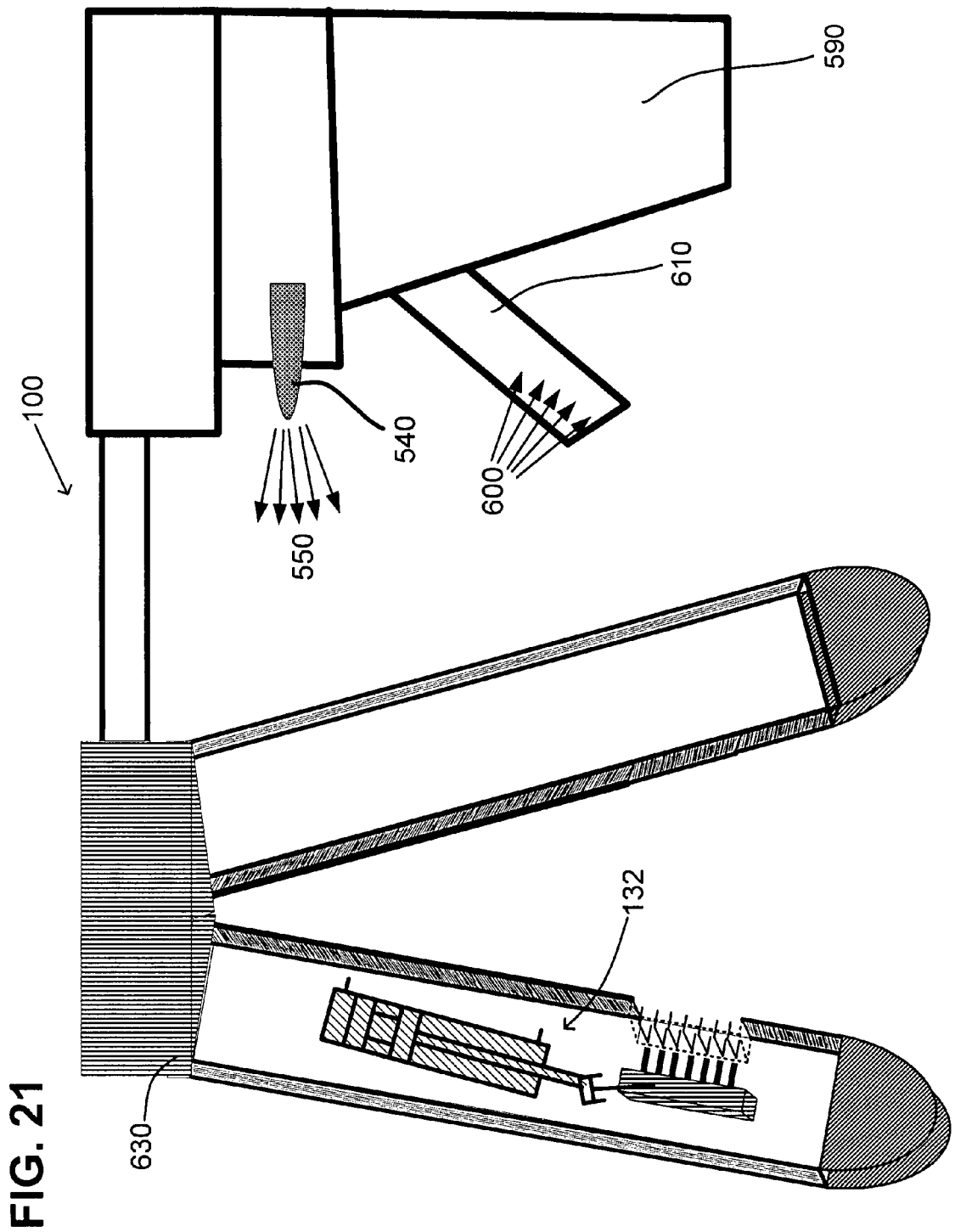
FIG. 21 is a schematic of a surgical instrument including an exemplary illustration of a force feedback signal.

FIG. 21 illustrates an embodiment of a surgical instrument 100 that includes a handgrip 590. The handgrip includes a trigger 610. The handgrip further includes a signal generator 540 that is capable of communicating signals 550. In an embodiment, the trigger/handgrip is adapted to receive one or more feedback signals 600 that may communicate to a human or robotic user information regarding the functional status of the surgical instrument. The signals may be, for example, generated by parts within the fastener/staple delivery mechanism 132. Those skilled in the art will appreciate that the term trigger includes, but is not limited to devices such as, push-button or lever or latch etc. Furthermore those skilled in the art will recognize that here the term "functional status" includes delivery status of surgical fasteners/staples (including whether a fastener or staple has been released by the instrument and whether the fastener/staple has been delivered into a bodily tissue in a correct or incorrect manner), number of staples/fasteners remaining in the surgical instrument, any defective surgical staples/fasteners in the surgical instrument, jammed surgical staples/fasteners or general malfunction of the surgical instrument. One skilled in the art will recognize that the feedback signals may include, inter alia, signals emanating as consequence of an operation of a fastener delivery mechanism 132.

Those skilled in the art will recognize that any type of feedback signal may be applied. Such signals may be optical, acoustic, provide force feedback, vibrational etc. The force feedback signal as shown in FIG. 21 is provided to the trigger and handle but it can be provided to any other area of the surgical instrument 100. The instrument may include such devices as an LED light, which may be disposed on the handle in easy view that responds to a feedback signal.

Figure 22:
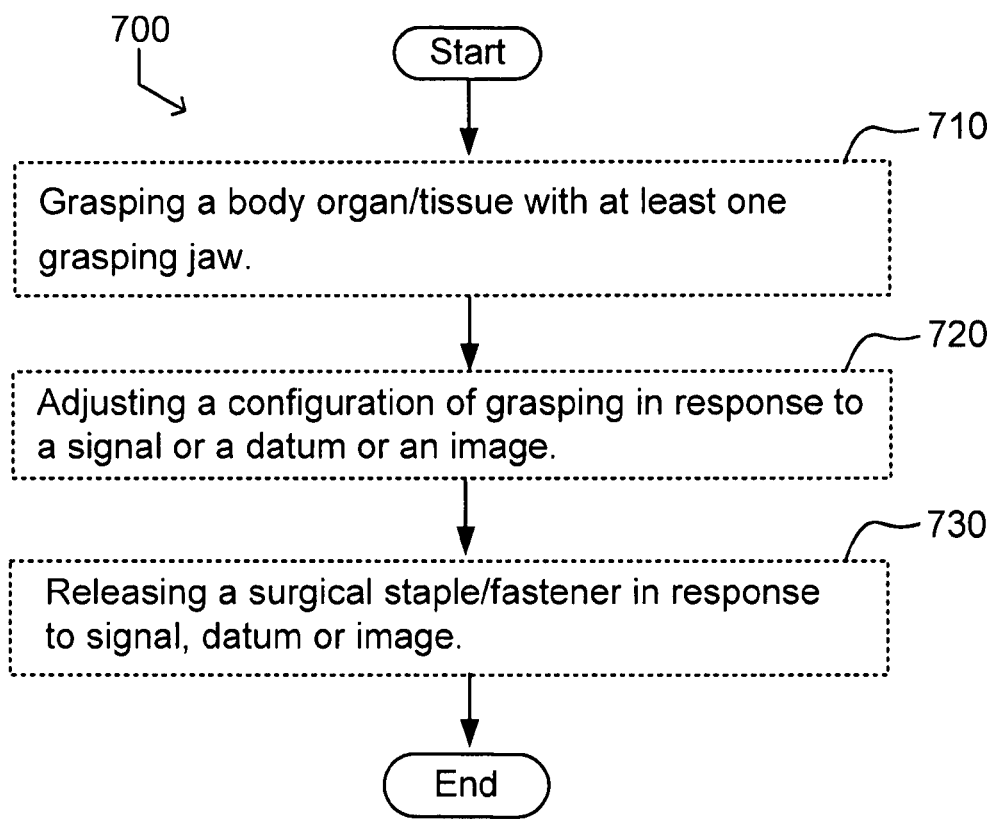
FIG. 22 illustrates embodiments of an exemplary operational flow for displaying an image.

In an embodiment illustrated in FIG. 22, an exemplary operation flow 700 for a method of splicing body organs/tissues comprises: grasping a body tissue with at least one grasping jaw 710; adjusting a configuration of the grasping in response to a signal or a datum or an image 720_provided by the instrument; and releasing a surgical staple/fastener in response to a signal, a datum or an image 730 provided by the instrument.

Figure 23:
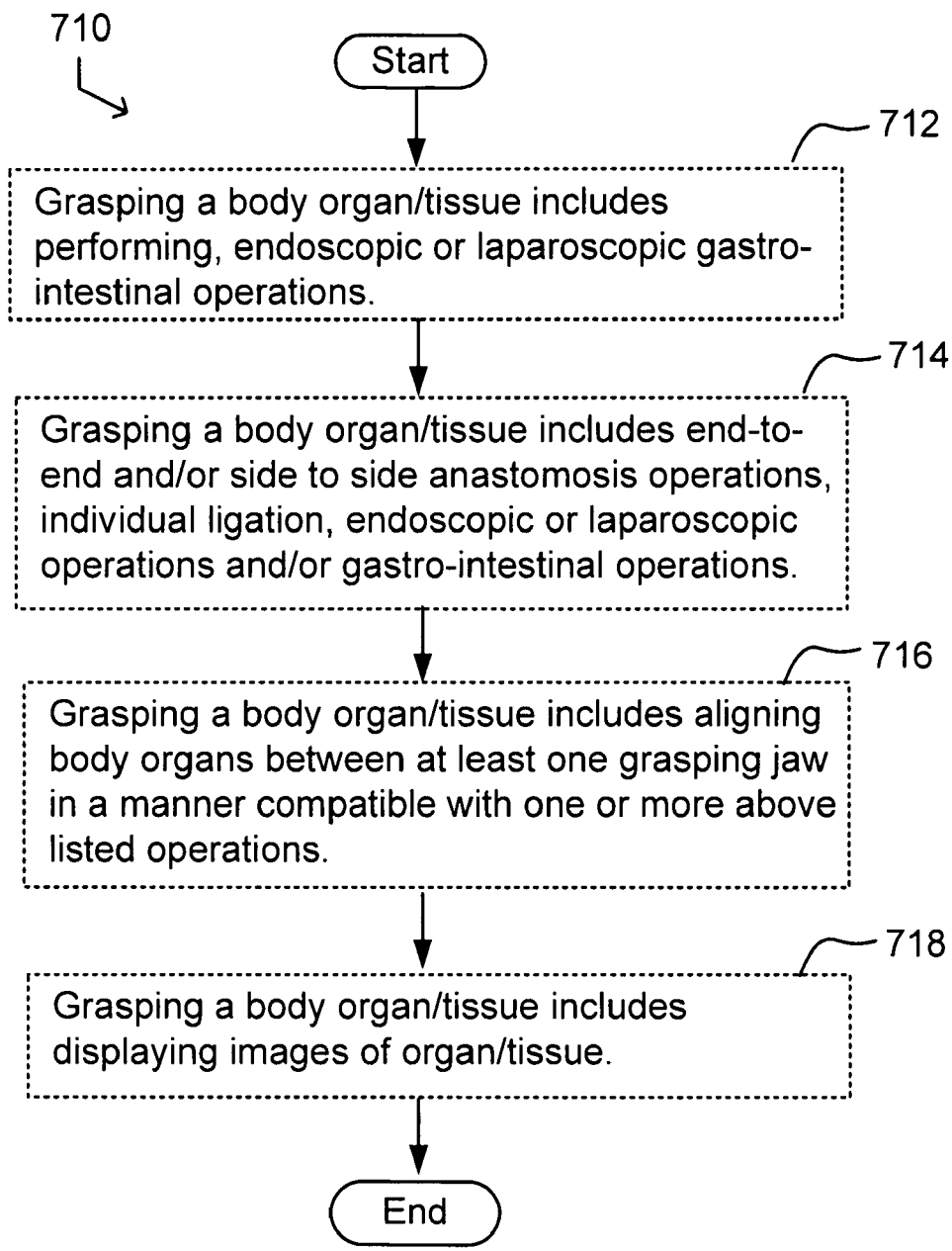
FIG. 23 illustrates embodiments of an exemplary operational flow for grasping a body organ or tissue.

As illustrated in FIG. 23, an exemplary operational flow for grasping a body tissue with at least one grasping jaw 710 may further include: performing endoscopic or laparoscopic gastro-intestinal operations 712; end-to-end or side to side anastomosis operations, individual ligation, endoscopic or laparoscopic operations or gastro-intestinal operations 714; aligning body organs between at least one grasping jaw in a manner compatible with one or more above listed operations 716; and displaying images of tissue 718.

Figure 24:
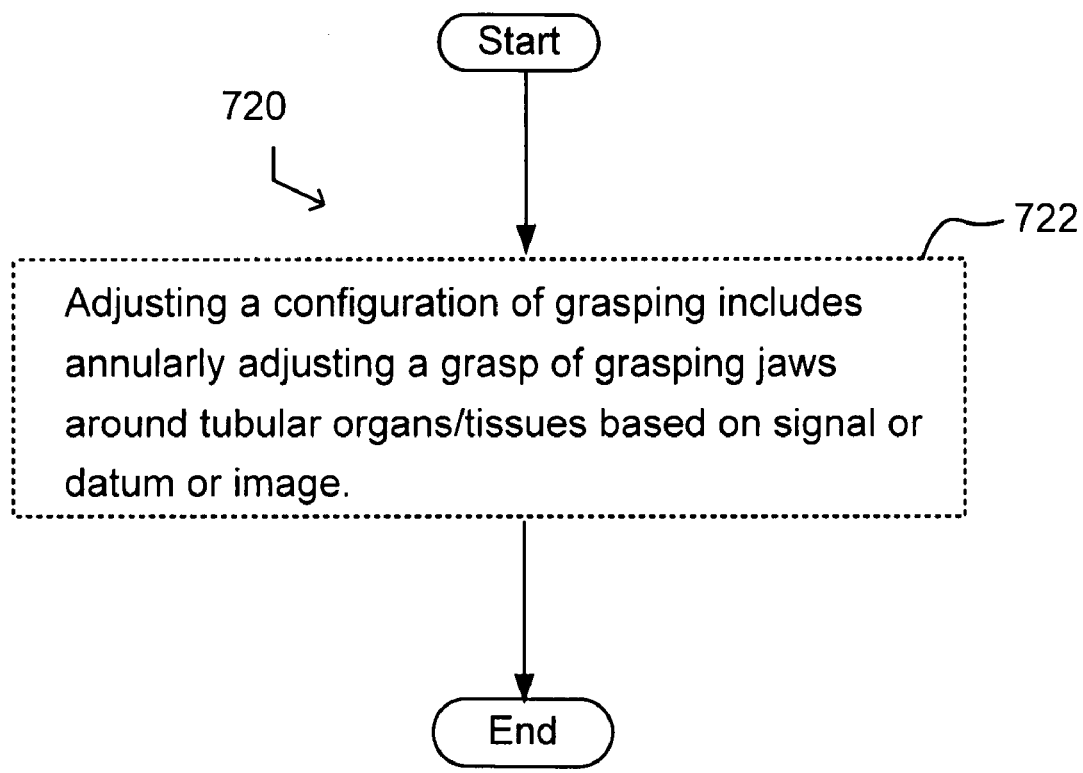
FIG. 24 illustrates embodiments of an exemplary operational flow for adjusting a configuration of grasping a body organ or tissue.

In an embodiment, there is illustrated in FIG. 24 an exemplary operational flow 720 for implementing a step of adjusting a configuration of grasping in response to a signal or a datum or an image. This step optionally includes annularly adjusting a grasp of grasping jaws around tubular organs/tissues based on signal or datum or image 722.

Figure 25:
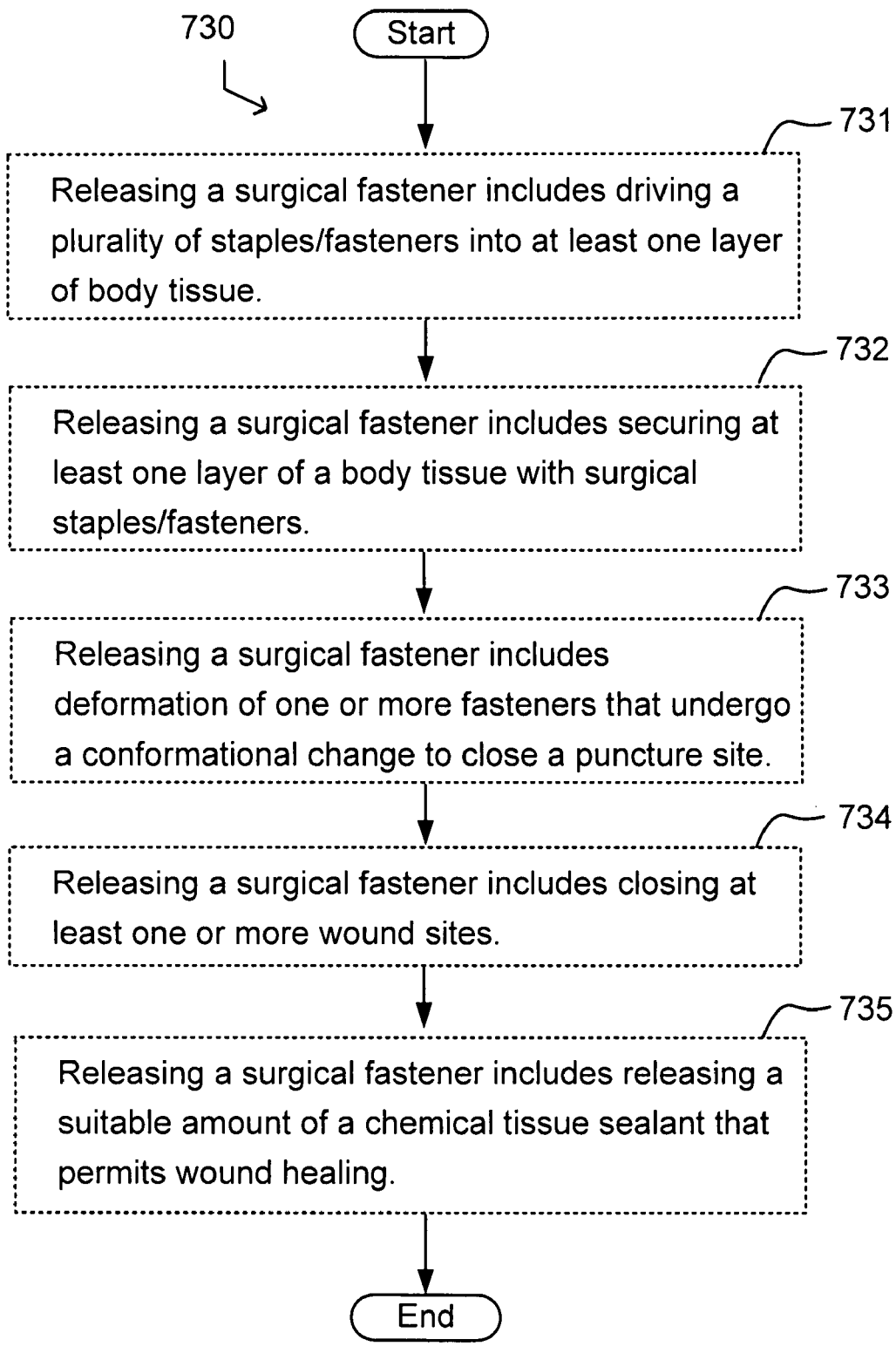
FIG. 25 illustrates embodiments of an exemplary operational flow for releasing a surgical fastener.

FIG. 25 shows another embodiment as provided by the instrument for releasing a surgical staple/fastener in response to signal, datum or image 730. This operation optionally includes the following exemplary steps: driving a plurality of staples/fasteners into at least one layer of body tissue 731; securing at least one layer of a body tissue with surgical staples/fasteners 732; deformation of one or more fasteners that undergo a conformational change to close a puncture site 733; closing at least one or more wound sites 734; and releasing a suitable amount of a chemical tissue sealant that permits wound healing 735.

Figure 26:
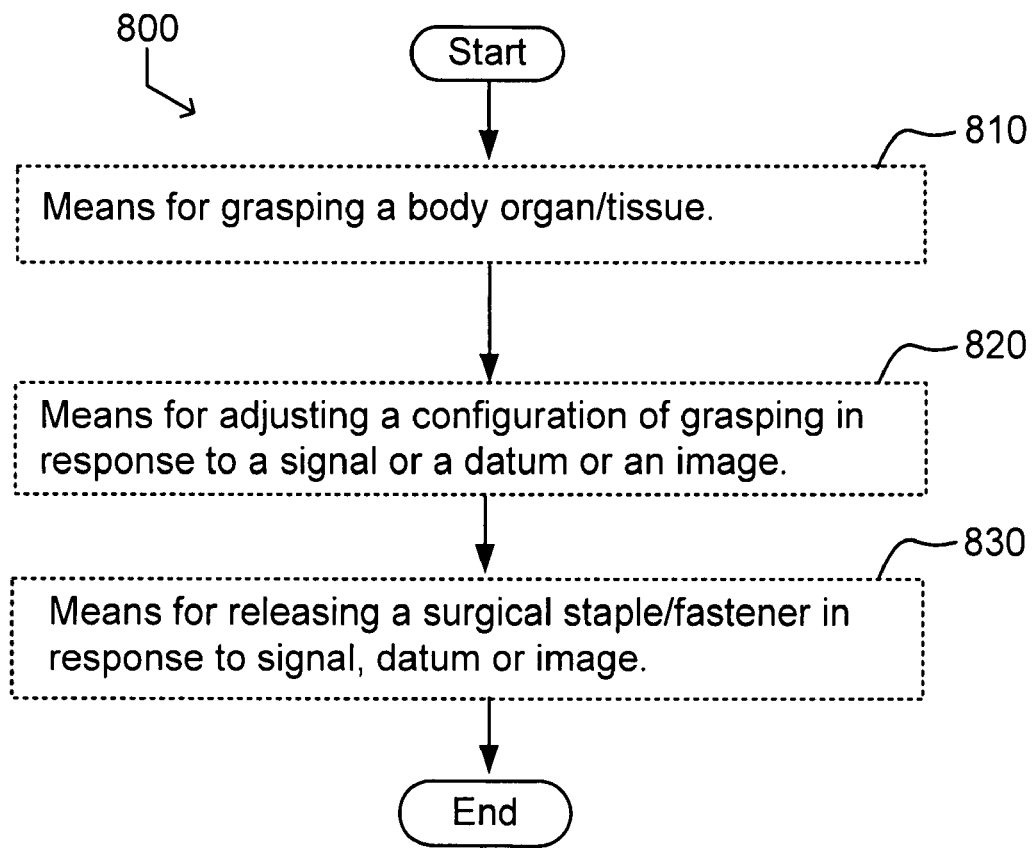
FIG. 26 illustrates embodiments for an exemplary surgical instrument.

As illustrated in FIG. 26, an embodiment of an exemplary surgical instrument includes: means for grasping a body tissue 810; means for adjusting a configuration of grasping in response to a signal or a datum or an image 820; means for releasing a surgical staple/fastener in response to signal, datum or image 830.

The foregoing detailed description has set forth various embodiments of the devices or processes via the use of flowcharts, diagrams, figures or examples. Insofar as such flowcharts, diagrams, figures or examples contain one or more functions or operations, it will be understood by those within the art that each function or operation within such flowchart, diagram, figure or example can be implemented, individually or collectively, by a wide range of any combination thereof.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

The herein described subject matter sometimes illustrates different components contained within, or connected with, different other components. It is to be understood that such depicted figures are merely exemplary, and that in fact many other figures can be implemented which achieve the same functionality. In a conceptual sense, any arrangement of components to achieve the same functionality is effectively "associated" or "coupled" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to, physically mateable or physically interacting components or wirelessly interactable or wirelessly interacting components or logically interacting or logically interactable components.

In a general sense, those skilled in the art will recognize that the various aspects described herein which can be implemented, individually or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes or devices described herein, or a microprocessor configured by a computer program which at least partially carries out processes or devices described herein), electrical circuitry forming a memory device (e.g., forms of random access memory), or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices or processes in the fashion set forth herein, and thereafter use engineering practices to integrate such described devices or processes into image processing systems. That is, at least a portion of the devices or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position or velocity; control motors for moving/distorting lenses to give desired focuses). A typical image processing system may be implemented utilizing any suitable commercially available components, such as those typically found in digital still systems or digital motion systems.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that a limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "operably coupled" or "coupled" or "in communication with" or "communicates with" or "operatively communicate" such other objects that the desired functionality is achieved. Hence, any two components herein combined to achieve a particular functionality can be seen as associated with each other such that the desired functionality is achieved, irrespective of architectures or intermedial components. Likewise, any two components so associated can also be viewed as being "connected", or "attached", to each other to achieve the desired functionality, and any two components capable of being so associated can also be viewed as being "operably couplable", to each other to achieve the desired functionality.

While particular aspects of the present subject matter described herein have been shown and described, it will be apparent to those skilled in the art that, based upon the embodiments herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). It will be further understood by those within the art that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B.

What is claimed is:

1. A surgical instrument comprising:
a flexually deformable and steerable shaft including at least one shape memory alloy, operably connected to at least one grasping jaw having a force generator mechanism that is contained within said at least one grasping jaw, said flexually deformable and steerable shaft being controllably deformable to permit a high degree of maneuverability of said surgical instrument.

2. The surgical instrument of claim 1, wherein said flexually deformable and steerable shaft is enclosed in a bendable and steerable tube or a sheath.

3. The surgical instrument of claim 1, wherein said at least one shape memory alloy includes at least one of titanium, nickel, zinc, copper, aluminum, cadmium, platinum, iron, manganese, cobalt, gallium or tungsten.

4. The surgical instrument of claim 1, wherein said at least one shape memory alloy is preconfigured to a particular application and to a body part geometry.

5. The surgical instrument of claim 1, wherein said at least one shape memory alloy assumes a different shape compared to an originally preconfigured shape to conform to an optimal orientation upon insertion of said surgical instrument into a body.

6. The surgical instrument of claim 1, wherein said shape memory alloy includes Nitinol™.

7. The surgical instrument of claim 1, wherein said at least one shape memory alloy includes electro-active polymer.

8. The surgical instrument of claim 1, wherein said at least one shape memory alloy includes at least one mechanically reconfigurable material.

9. The surgical instrument of claim 1, wherein said flexually deformable and steerable shaft being controllably deformable to permit a high degree of maneuverability of said surgical instrument includes controllable deformation of said shaft that is mediated by at least one of a temperature profile, a pressure profile, an electrical circuitry, a magnetic profile, an acoustic wave profile or an electro-magnetic radiation profile.

10. The surgical instrument of claim 1, wherein said flexually deformable and steerable shaft being controllably deformable to permit a high degree of maneuverability of said surgical instrument includes maneuverability and steerability of said surgical instrument around anatomical corners or difficult-to-reach anatomical body parts that are normally inaccessible on a straight trajectory.

11. The surgical instrument of claim 1, wherein said flexually deformable and steerable shaft being controllably deformable to permit a high degree of maneuverability of said surgical instrument includes bending said shaft in real time to navigate within a body space.

12. The surgical instrument of claim 1, wherein said flexually deformable and steerable shaft returns to an original shape or configuration for easy removal of said surgical instrument from a body.

13. The surgical instrument of claim 1, wherein said surgical instrument is a surgical stapler that is adapted to deliver staples, fasteners, pins or ties.

14. The surgical instrument of claim 1, further comprising at least one grasping jaw having a proximity detector.

15. The surgical instrument of claim 14, wherein said proximity detector is adapted to detect whether a biological tissue is partly within grasping distance of said grasping jaw.

16. The surgical instrument of claim 14, wherein said proximity detector is adapted to detect whether a biological tissue is fully within grasping distance of said grasping jaw.

17. The surgical instrument of claim 14, wherein said proximity detector is operably configured to assess whether an entire organ or a portion of a bodily organ is fully or partly grasped within said grasping jaw.

18. The surgical instrument of claim 1, further comprising at least one grasping jaw that is fully redeployable following at least one grasp-and-release cycle in a grasping operation of a biological tissue or bodily organ.

19. The surgical instrument of claim 1, further comprising at least one grasping jaw that is independently maneuverable from an attached shaft or a sheath.

20. The surgical instrument of claim 1, wherein said at least one grasping jaw is configured to movably operate in an opposing manner with respect to at least one other grasping jaw.

21. The surgical instrument of claim 1, wherein said at least one grasping jaw is configured to operably mate with at least one other grasping jaw.

22. The surgical instrument of claim 1, wherein said at least one grasping jaw is configured to serve as an anvil for forming an interaction surface between at least one surgical staple and bodily tissues, said forming being facilitated by reversible mating and unmating of said anvil with an opposite grasping jaw.

23. The surgical instrument of claim 1, wherein said at least one grasping jaw forms an annular grasp around a body tissue.

* * * * *